US010196520B2

(12) United States Patent
Pratt et al.

(10) Patent No.: US 10,196,520 B2
(45) Date of Patent: Feb. 5, 2019

(54) DIRECT DYES AND COMPOSITION COMPRISING THE DYES

(71) Applicant: KAO GERMANY GMBH, Darmstadt (DE)

(72) Inventors: Dominic Pratt, Darmstadt (DE); Hartmut Möhring, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 8 days.

(21) Appl. No.: 15/538,095

(22) PCT Filed: Dec. 11, 2015

(86) PCT No.: PCT/EP2015/079372
§ 371 (c)(1),
(2) Date: Jun. 20, 2017

(87) PCT Pub. No.: WO2016/102207
PCT Pub. Date: Jun. 30, 2016

(65) Prior Publication Data
US 2017/0362436 A1 Dec. 21, 2017

(30) Foreign Application Priority Data

Dec. 22, 2014 (EP) .................................. 14199839

(51) Int. Cl.
C09B 29/033 (2006.01)
C09B 29/36 (2006.01)
A61K 8/41 (2006.01)
A61K 8/49 (2006.01)
A61Q 5/06 (2006.01)

(52) U.S. Cl.
CPC .......... C09B 29/0092 (2013.01); A61K 8/416 (2013.01); A61K 8/49 (2013.01); A61K 8/4986 (2013.01); A61Q 5/065 (2013.01); C09B 29/0055 (2013.01); C09B 29/0059 (2013.01); C09B 29/0066 (2013.01); C09B 29/0074 (2013.01); C09B 29/0081 (2013.01); C09B 29/0085 (2013.01); C09B 29/3682 (2013.01)

(58) Field of Classification Search
CPC ...... A61Q 5/065; A61K 8/416; A61K 8/4986; C09B 29/0081; C09B 29/0092; C09B 29/0085; C09B 29/0055; C09B 29/0059; C09B 29/009829; C09B 29/0066; C09B 29/0074; C09B 29/3682
See application file for complete search history.

(56) References Cited

U.S. PATENT DOCUMENTS 5,342,928 A  8/1994 Roetsch et al.

FOREIGN PATENT DOCUMENTS

| EP | 0 569 759 A1 | 11/1993 | |
| EP | 1 369 105 A1 | 12/2003 | |
| FR | 2 954 133 A1 | 6/2011 | |
| JP | 04-292988 | * 10/1992 | ............. B41M 5/30 |
| JP | 3 005821 B2 | 2/2000 | |

OTHER PUBLICATIONS

STIC Search Report (Inventors Search) dated Oct. 3, 2017.*
STIC Search Report (Formula 1) dated Oct. 3, 2017.*
International Search Report dated Jan. 27, 2016, dated Feb. 4, 2016.

* cited by examiner

Primary Examiner — Eisa B Elhilo
(74) Attorney, Agent, or Firm — Norris McLaughlin, PA

(57) ABSTRACT

The present invention relates to novel direct dyes and compositions comprising them for dyeing keratin fibers especially human hair. The novel dyes of the present invention have benzothiophene structure providing intensive and homogeneous dyeing on keratin fibers, especially human hair.

15 Claims, No Drawings

DIRECT DYES AND COMPOSITION COMPRISING THE DYES

This application is the U.S. National Stage of International Application No. PCT/EP2015/079372, filed Dec. 11, 2015, which claims foreign priority benefit under 35 U.S.C. § 119 of European Application No. 14199839.3 filed Dec. 22, 2014.

Hair dyes have been known for many decades and are classified into two main categories as direct and oxidative dyes. Direct dyes are usually used to achieve temporary colors on keratin fibers. They usually exhibit variable dyeing ability and also considerably changing durability on hair. On the other hand, homogeneity of the colors obtained on the keratin fibers is also very much variable and generally speaking, intensive but less durable on damaged hair, whereas colors on natural hair are less intensive but more durable. In other words, there are problem associated with intensive and homogeneous coloring of keratin fibers, especially human hair, with direct dyes.

Direct dyes are also classified according to their ionic change such as cationic, anionic and neutral dyes. Cationic and nonionic dyes are mostly used for coloring keratin fibers and there are many commercialized products on the hair coloring market from various suppliers. However, recently, hair dyeing composition is made commercially available comprising anionic dyes. EP1369105 discloses various novel direct dyes and the compositions comprising them for coloring human hair.

The problems associated with dyeing hair using direct dyes have not yet been completely solved and especially there are still needs for realizing intensive and homogeneous dyeing on hair fibers comprising various parts with various degree of hair damage. Such problems are even aggravated in coloring hair into red or shades comprising high level of red.

The aim of the present invention is to provide novel dyes for coloring keratin fibers intensively and homogeneously. In particular, the aim of the present invention is to provide novel dyes for coloring keratin fibers, especially human hair, comprising damaged and undamaged parts intensively and homogeneously.

The inventors of the present invention have found out that the special novel dyes having benzothiophene structure providing intensive and homogeneous dyeing on keratin fibers, especially human hair.

Accordingly, the first object of the present invention is the compounds according to the general structure

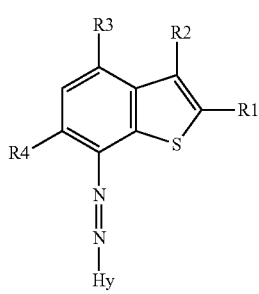

wherein $R_1$ is H, $C_1$-$C_4$ alkyl, $C_1$-$C_4$ hydroxyalkyl, COOH or COOR$_5$ wherein R$_5$ is $C_1$-$C_4$ alkyl, $R_2$ is H or NR$_6$R$_7$ wherein $R_6$ and $R_7$ are same or different H, $C_1$-$C_4$alkyl, $C_1$-$C_4$ hydroxyalkyl or acetyl, $R_3$ is H, OH, NR$_6$R or NHSO$_2$R$_8$ wherein R$_8$ is NR$_6$R alkyl or NR$_6$R hydroxyalkyl, $R_4$ is H, COOH or COOR$_5$ and Hy is any heterocyclic group which is bound at a C atom to the diazo group and which may be substituted or unsubstituted.

In a preferred embodiment of the present invention, Hy is preferably selected from the following structures:

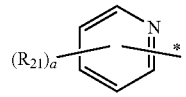
A-1

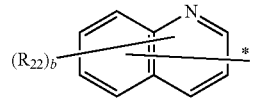
A-2

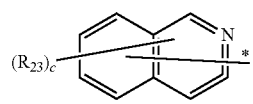
A-3

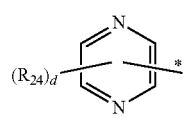
A-4

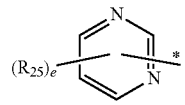
A-5

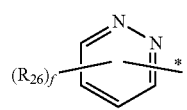
A-6

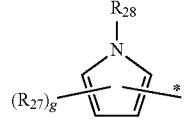
A-7

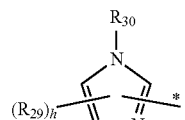
A-8

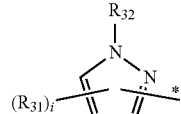
A-9

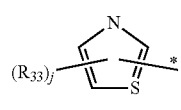
A-10

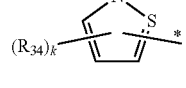
A-11

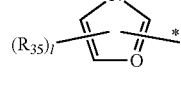
A-12

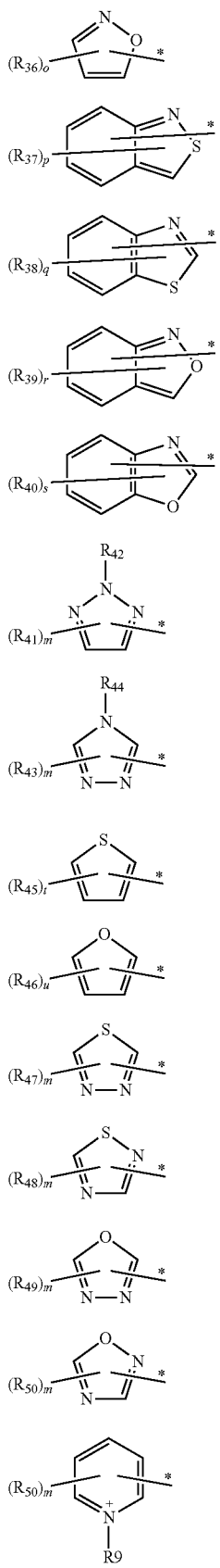

wherein $R_9$ is $C_1$-$C_4$ alkyl or $C_1$-$C_4$ hydroxyalkyl and "*" expresses position at which group binds to the diazo group, $R_{21}$ to $R_{50}$ independently represent hydrogen atom or a substituent which is selected from halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; more preferably the substituent is halogen atom, alkyl group, cyano group, hydroxyl group, nitro group, alkoxy group, amino group (including anilino group), acylamino group, alkylsulfonylamino group, and carbamoyl group, "a, p, q, r, s" represent an integer of 0 to 4, "b, c" represent an integer of 0 to 6, "d, e, f, g, t, u" represent an integer of 0 to 3, "h, i, j, k, l, o" represent an integer of 0 to 2, "m" represent an integer of 0 to 1, when "a" to "u" represent an integer of 2 or more, groups represented by $R_{21}$ to $R_{50}$, which exist in a number of 2 or more, may be the same or different to each other.

In the compound represented by the general formula (1) in accordance with the invention, the hetero-ring group is preferably (A-1), (A-5), (A-8), (A-9), (A-10), (A-11), (A-12), (A-13), (A-14), (A-15), (A-17), (A-19), (A-22), (A-23), (A-24), (A-25) and (A-26) more preferably (A-10), (A-11), (A-12), (A-14), (A-22), (A-23), (A-25) and (A-26), and particularly preferably (A-10), (A-23) and (A-26).

Following dyes are the preferred individual compounds within the scope of the present inventions.

D-1

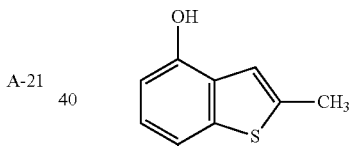

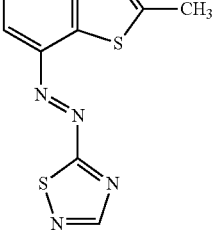

D-2

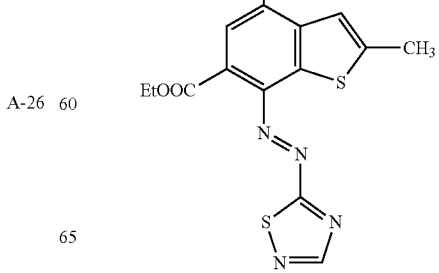

-continued
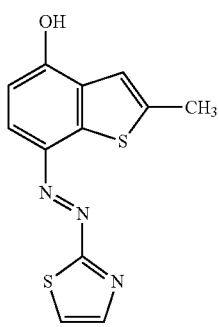
D-3
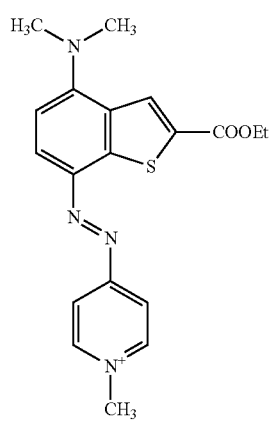
D-4
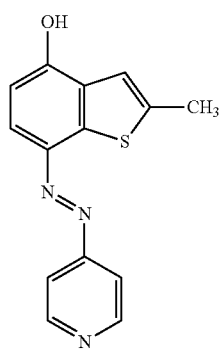
D-5
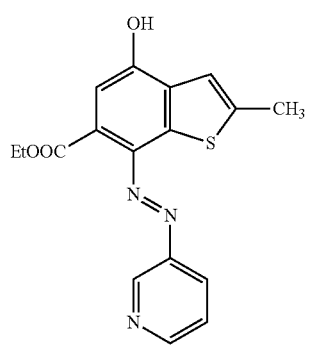
D-6
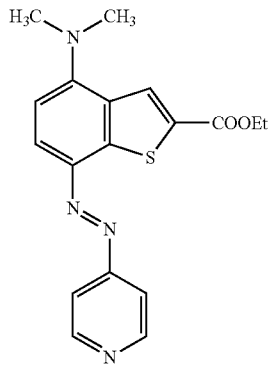
D-7
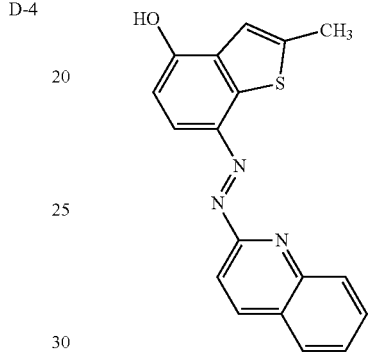
D-8
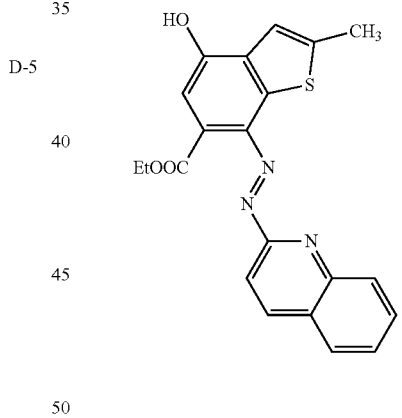
D-9
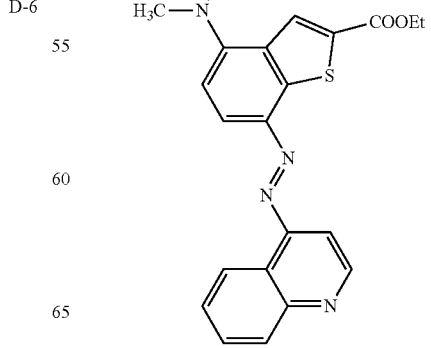
D-10

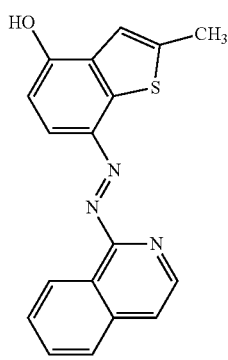
D-11
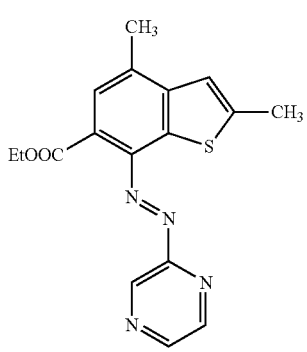
D-15
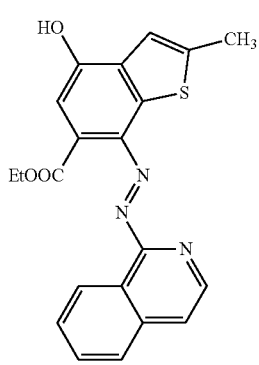
D-12
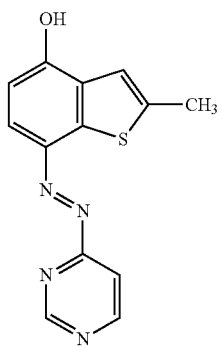
D-16
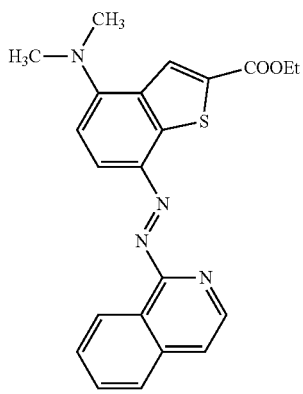
D-13
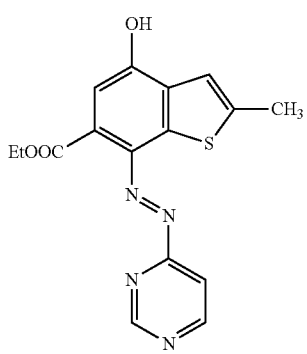
D-17
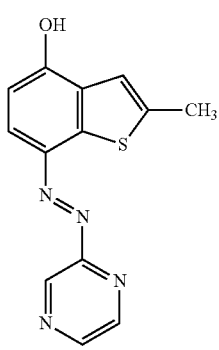
D-14
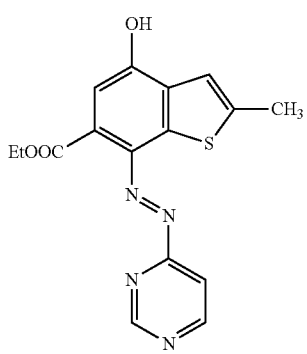
D-18

-continued
D-19
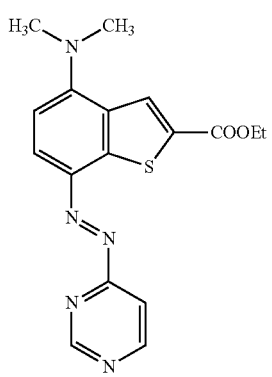
D-20
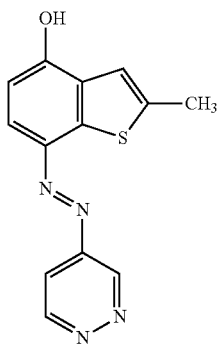
D-21
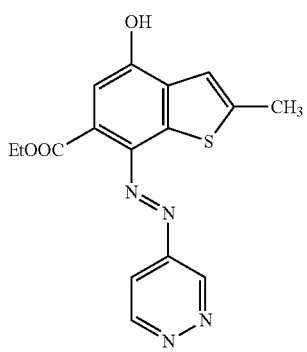
D-22
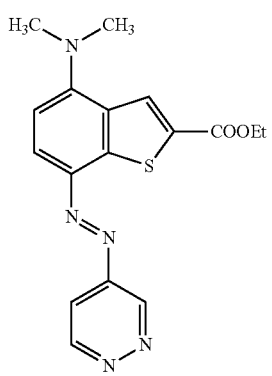
-continued
D-23
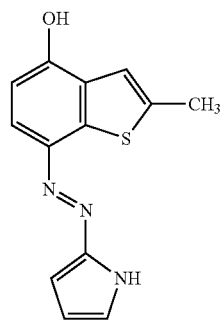
D-24
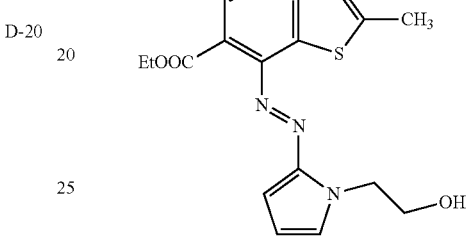
D-25
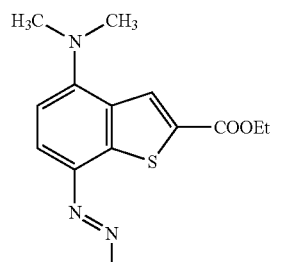
D-26
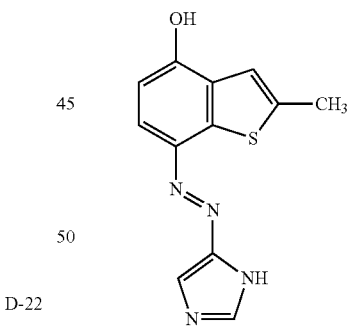
D-27
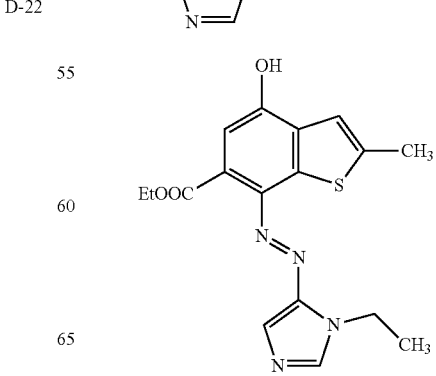

-continued
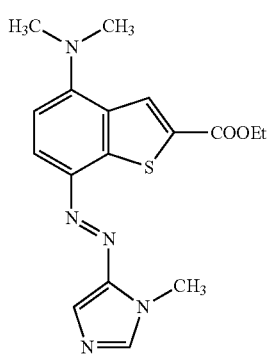
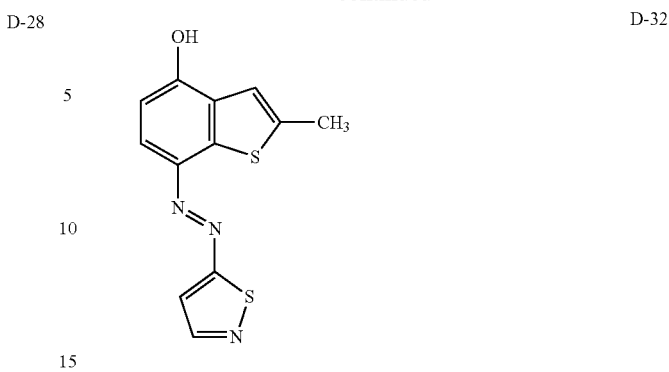
D-28
D-32
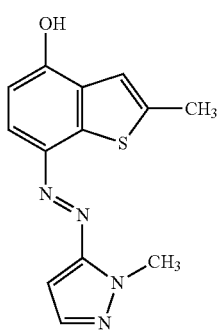
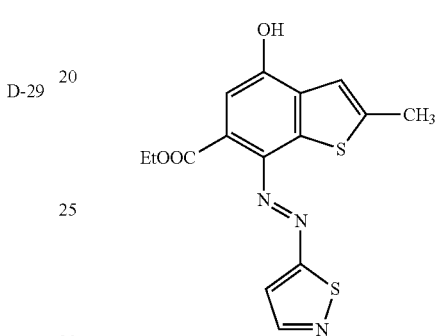
D-29
D-33
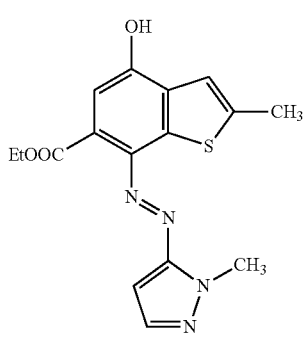
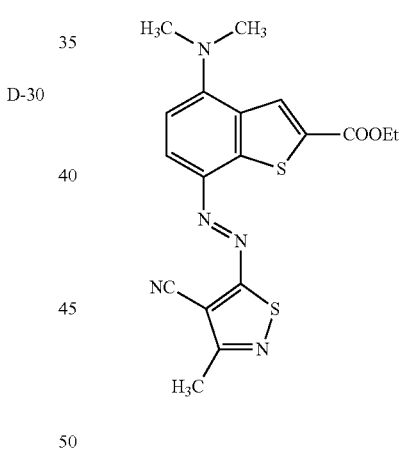
D-30
D-34
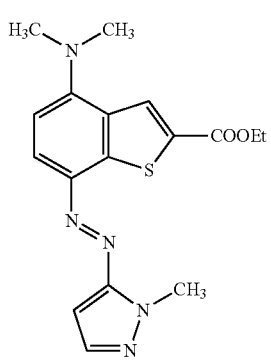
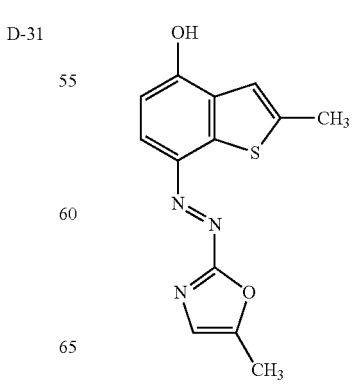
D-31
D-35

-continued
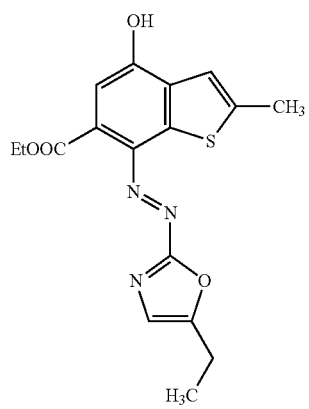
D-36
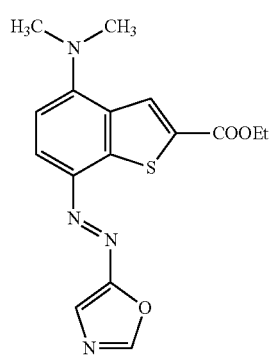
D-37
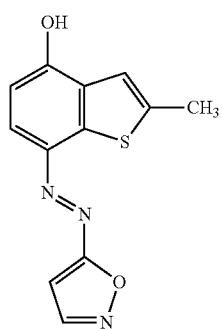
D-38
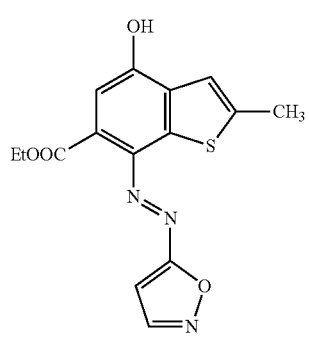
D-39
-continued
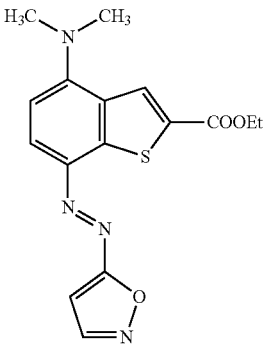
D-40
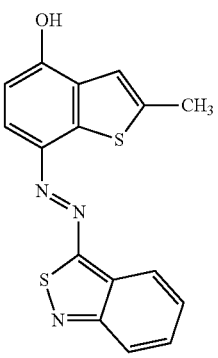
D-41
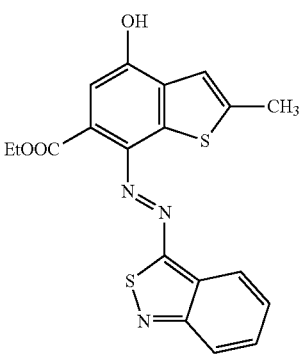
D-42
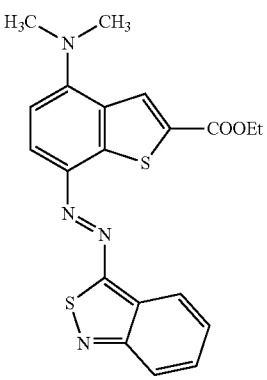
D-43

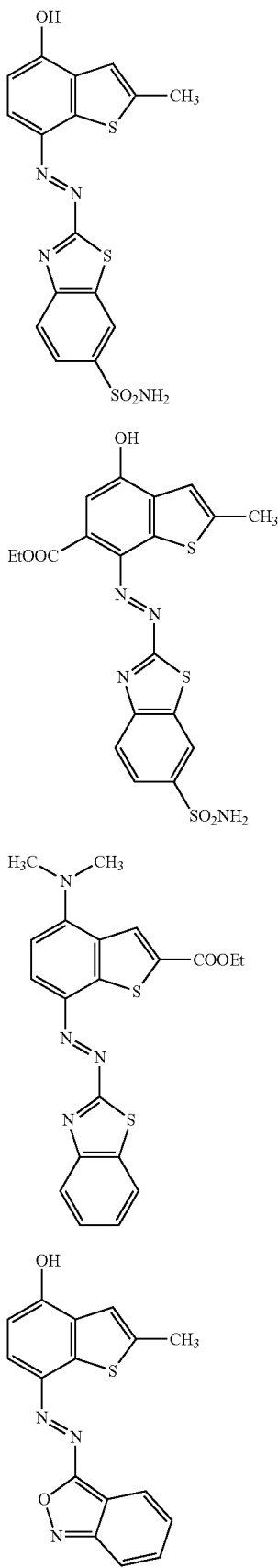
D-44
D-45
D-46
D-47
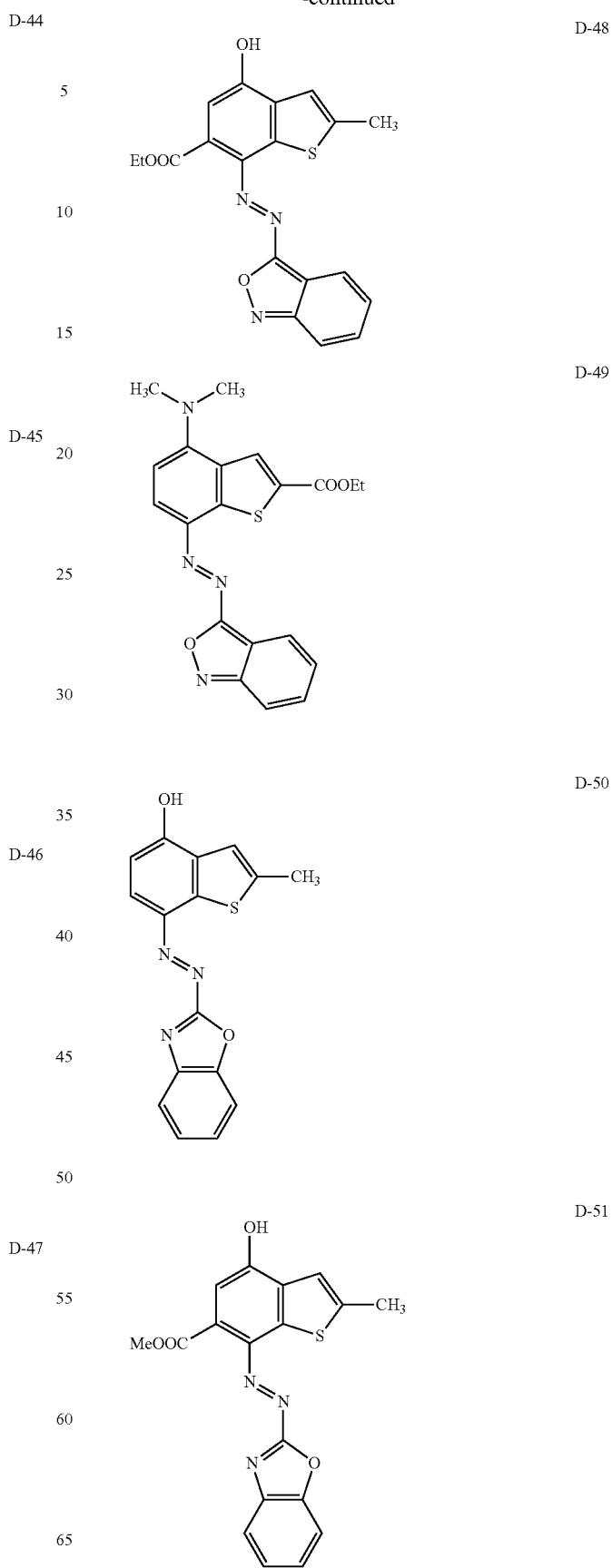
D-48
D-49
D-50
D-51

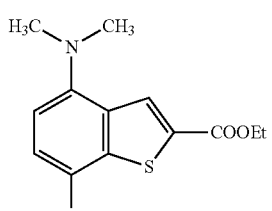
D-52
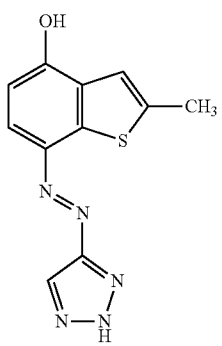
D-53
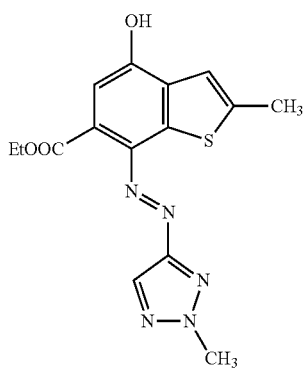
D-54
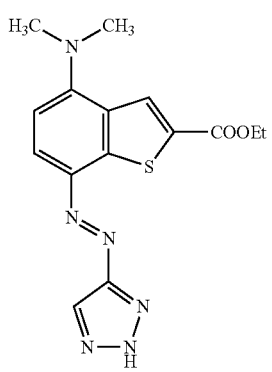
D-55
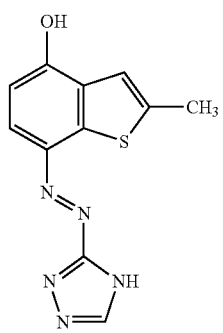
D-56
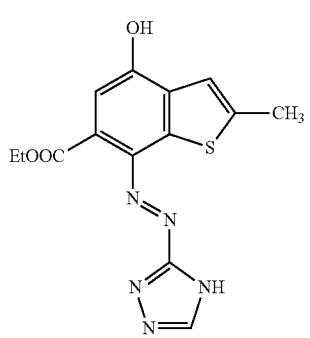
D-57
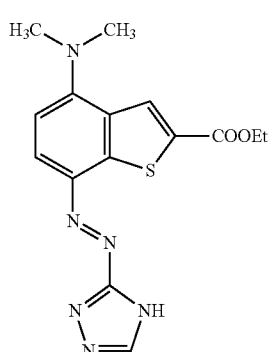
D-58
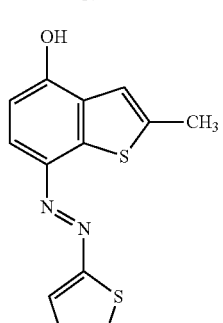
D-59
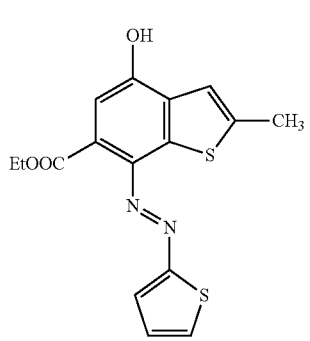
D-60

D-61 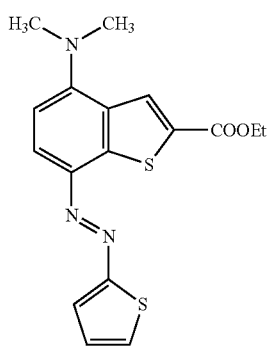
D-62 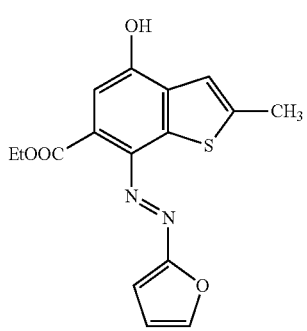
D-63 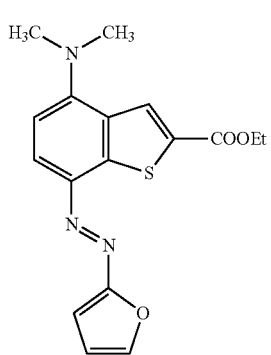
D-64 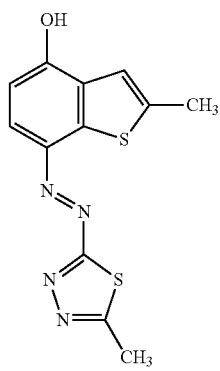
D-65 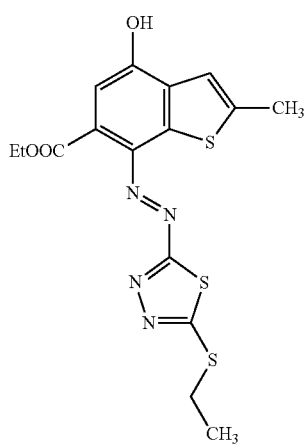
D-66 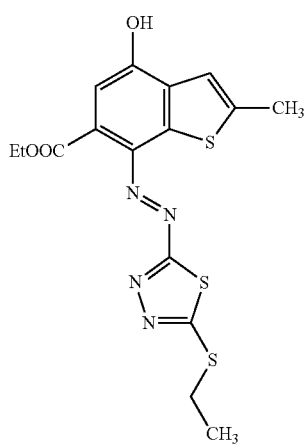
D-67 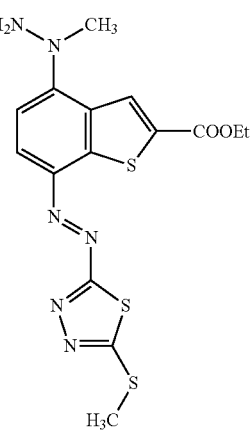
D-68 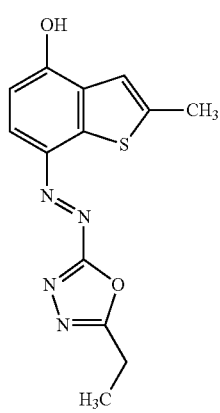

D-69 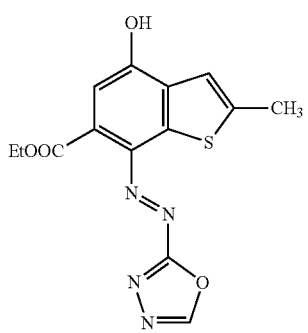
D-70 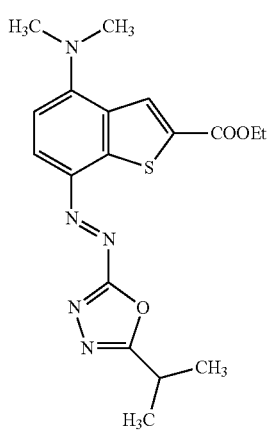
D-71 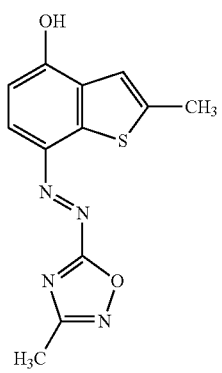
D-72 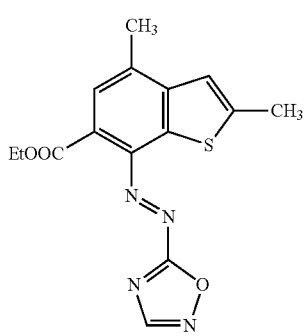
D-73 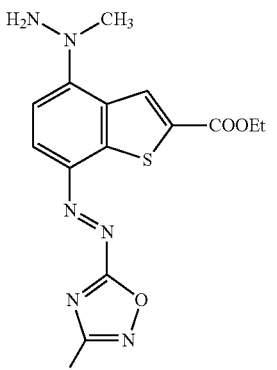
D-74 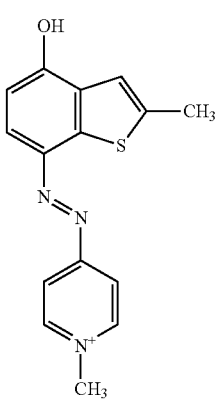
D-75 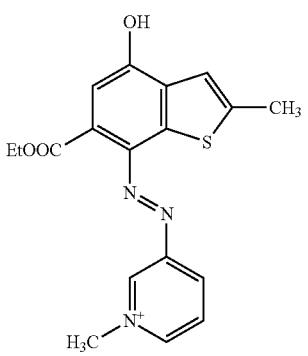
D-76 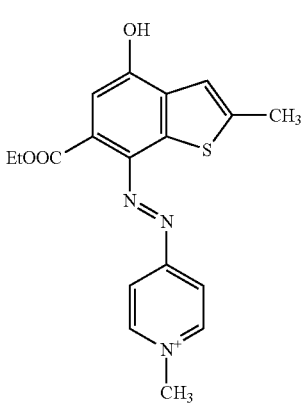
The preferred are compounds D-1, D-2, D-3 and D4. The most referred ones are D-2 and D-3.
The second object is the use of the above compounds for coloring keratin fibers, especially human hair.

The third object is a composition comprising one or more of the above disclosed dye compounds.

The fourth object is the use of a composition comprising one or more of the above dye compounds for colouring keratin fibers especially human hair.

The above compounds are comprised in the compositions at a concentration in the range of 0.0001 to 10%, preferably 0.001 to 7.5%, more preferably 0.01 to 5% and most preferably 0.02 to 4% by weight, calculated to the total of the composition.

The compositions comprising the compounds may further comprise additional compounds such as surfactants, thickening polymers, conditioning agents, solvents, fatty substances such as fatty alcohols, and oils.

The composition may be in the form of a solution, an emulsion or gel. The dye compounds may as well be comprised in a bleaching composition in powder form and comprise additionally hair bleaching powder compounds such as persalts for example persulfate salts of sodium, potassium and ammonium.

Surfactants suitable for the purpose are anionic, nonionic, cationic and amphoteric ones.

Suitable anionic surfactants are of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

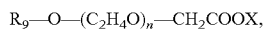

$R_9$—O—$(C_2H_4O)_n$—$CH_2COOX$, wherein $R_9$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted.

Further suitable anionic surfactants are also $C_8$-$C_{22}$-acyl aminocarboxylic acids or the water-soluble salts thereof, such as N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in mixture with the above-named anionic surfactants.

Suitable non-ionic surfactants are alkyl polyglucosides of the general formula

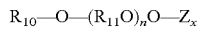

$R_{10}$—O—$(R_{11}O)_n$O—$Z_x$ wherein $R_{10}$ is an alkyl group with 8 to 18 carbon atoms, $R_{11}$ is an ethylene or propylene group, Z is a saccharide group with 5 to 6 carbon atoms, n is a number from 0 to 10 and x is a number between 1 and 5. Examples are decyl polyglucoside, cocoyl polyglucoside both are commercially available.

Further nonionic surfactant components are, for example, long-chain fatty acid mono- and dialkanolamides, such as coco fatty acid monoethanolamide and myristic fatty acid monoethanolamide.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$".

Further nonionic surfactants as emulsifiers useful in the compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 50, preferably about 10 and about 30.

Among the non-ionic surfactants mentioned above fatty alcohol ethoxylates are the most preferred ones. Above mentioned non-ionic surfactants can also be used as mixture of one category such as several ethoxylated fatty alcohols or several categories such as mixture of alkyl polyglucoside and ethoxylated fatty alcohol.

As further surfactant suitable for the compositions according to the present invention are amphoteric or zwitterionic surfactants. Useful as such are in particular the various known betaines such as alkyl betaines such as cocoyl betaine, fatty acid amidoalkyl betaines such as cocamidopropyl betaine and sulfobetaines, for example, lauryl hydroxysulfobetaine; long-chain alkyl amino acids, such as cocoaminoacetate, cocoaminopropionate and sodium cocoamphopropionate and -acetate.

Further suitable surfactants are cationic surfactants according to general formula

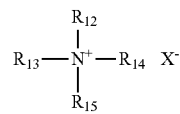

where $R_{12}$ is saturated or unsaturated, branched or straight alkyl chain with 8-22 C atoms or

$R_{16}CO$ $NH(CH_2)_n$ where $R_{16}$ is saturated or unsaturated, branched or straight alkyl chain with 7-21 C atoms and n has typical value of 1-4 or

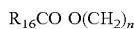

$R_{16}CO$ $O(CH_2)_n$ where $R_{16}$ is saturated or unsaturated, branched or straight alkyl chain with 7-21 C atoms and n has typical value of 1-4, and $R_{13}$ is a saturated or unsaturated, branched or straight alkyl chain with 1-22 C atoms or

$R_{16}CO$ $NH(CH_2)_n$ where $R_{16}$ is saturated or unsaturated, branched or straight alkyl chain with 7-21 C atoms and n has typical value of 1-4 or

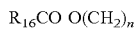

$R_{16}CO$ $O(CH_2)_n$ where $R_{16}$ is saturated or unsaturated, branched or straight alkyl chain with 7-21 C atoms and n has typical value of 1-4, and $R_{14}$ and $R_{15}$ are independent from each other lower alkyl chain with 1 to 4 carbon atoms or ethoxy or propoxy group with number of ethoxy or propoxy groups varying in the range of 0 to 4, and X is chloride, bromide or methosulfate.

Suitable cationic surfactants are, for example, long-chain quaternary ammonium compounds which can be used alone or in mixture with each other, such as cetyl trimethyl ammonium chloride, myristoyl trimethyl ammonium chloride, behentrimonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, stearamidopropyldimethylamoonium chloride, dipalmitoyl dimonium chloride, distearyl dimethyl ammonium chloride, stearamidopropyl trimonuim chloride.

Further examples to the cationic surfactants are so called esterquats available on the market, for example, under the trade names "Schercoquat®", "Dehyquart® L80" and "Tetranyl®". Still further examples are so called amidoquats again available on the market, for example, under the trade name "INCROQUAT$^a$ HO" or "OCS".

Total surfactant concentration varies between 0.1 and 25%, preferably 0.2 and 20%, and more preferably 0.5 to 15% and most preferably 0.5 to 15% by weight calculated to total of the composition.

The compositions may comprise one or more hair conditioning compound. Conditioners may be comprised in the compositions at a concentration in the range of 0.01 to 15%, preferably 0.05 to 10%, and more preferably 0.1% to 5% by weight calculated to the total of the composition.

Examples of the conditioning component generally include cationic polymers, silicones, fatty alcohols, and conditioning oils (for example, hydrocarbon oil, polyolefin and fatty acid ester) and their mixtures. The composition may comprise a single type of conditioning component, or two or more in combination.

Suitable cationic polymers are copolymer of a diallyl quaternary ammonium salt include dimethyldiallylammonium chloride polymer (polyquaternium-6, for example, MERQUAT 100; Nalco Company), dimethyldiallylammonium chloride/acrylic acid copolymer (polyquaternium-22, for example, MERQUAT 280, MERQUAT 295; Nalco Company), and dimethyldiallylammonium chloride/acrylic acid amide copolymer (polyquaternium-7, for example, MERQUAT 550; Nalco Company).

Specific examples of the quaternized polyvinylpyrrolidone include quaternary ammonium salts synthesized from a copolymer of vinylpyrrolidone (VP) and dimethylaminoethyl methacrylate, and diethyl sulfate (polyquaternium 11, for example, GAFQUAT 734, GAFQUAT 755 and GAFQUAT 755N (all by ISP Japan, Ltd.)).

Specific examples of the cationized cellulose include a polymer of a quaternary ammonium salt obtained by adding glycidyltrimethylammonium chloride to hydroxyethylcellulose (polyquaternium-10, for example, RHEOGUARD G and RHEOGUARD GP (all by Lion Corp.), POLYMER JR-125, POLYMER JR-400, POLYMER JR-30M, POLYMER LR-400 and POLYMER LR-30M (all by Amerchol Corp.)), and a hydroxyethylcellulose/dimethyldiallylammonium chloride copolymer (polyquaternium-4, for example, CELQUAT H-100, CELQUAT L-200 (all by National Starch and Chemical Company)).

Cationic polymers may be comprised in the compositions at a concentration in the range of 0.01 to 5%, preferably 0.05 to 4%, and more preferably 0.1% to 2.5% by weight calculated to the total of the composition.

The compositions may comprises one or more silicone. Examples of the silicone include dimethylpolysiloxane, and modified silicone (for example, amino-modified silicone, fluorine-modified silicone, alcohol-modified silicone, polyether-modified silicone, epoxy-modified silicone, or alkyl-modified silicone), but dimethylpolysiloxane, polyether-modified silicone and amino-modified silicone are preferred.

The dimethylpolysiloxane may be any cyclic or non-cyclic dimethylsiloxane polymer, and examples thereof include SH200 series, BY22-019, BY22-020, BY11-026, B22-029, BY22-034, BY22-050A, BY22-055, BY22-060, BY22-083, FZ-4188 (all by Dow Corning Toray Co., Ltd.), KF-9008, KM-900 series, MK-15H, and MK-88 (all by Shin-Etsu Chemical Co., Ltd.).

The polyether-modified silicone may be any silicone having a polyoxyalkylene group, and the group constituting the polyoxyalkylene group may be an oxyethylene group or an oxypropylene group. More specific examples include KF-6015, KF-945A, KF-6005, KF-6009, KF-6013, KF-6019, KF-6029, KF-6017, KF-6043, KF-353A, KF-354A, KF-355A (all by Shin-Etsu Chemical Co., Ltd.), FZ-2404, SS-2805, FZ-2411, FZ-2412, SH3771M, SH3772M, SH3773M, SH3775M, SH3749, SS-280X series, BY22-008 M, BY11-030, and BY25-337 (all by Dow Corning Toray Co., Ltd.).

The amino-modified silicone may be any silicone having an amino group or an ammonium group, and examples thereof include an amino-modified silicone oil having all or a part of the terminal hydroxyl groups capped with a methyl group or the like, and an amodimethicone which does not have the terminals capped. A preferred example of the amino-modified silicone may be a compound represented by the following formula:

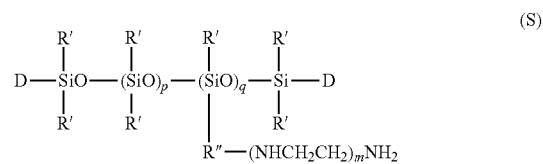

(S)

wherein R' represents a hydroxyl group, a hydrogen atom or $R^X$; $R^X$ represents a substituted or unsubstituted monovalent hydrocarbon group having 1 to 20 carbon atoms; D represents $R^X$, R"—$(NHCH_2CH_2)_mNH_2$, $OR^X$, or a hydroxyl group; R" represents a divalent hydrocarbon group having 1 to 8 carbon atoms; m represents a number from 0 to 3; p and q represent numbers, the sum of which is, as a number average, equal to or greater than 10 and less than 20,000, preferably equal to or greater than 20 and less than 3000, more preferably equal to or greater than 30 and less than 1000, and even more preferably equal to or greater than 40 and less than 800.

Specific examples of suitable commercially available products of the amino-modified silicone include amino-modified silicone oils such as SF8452C, SS-3551 (all by Dow Corning Toray Co., Ltd.), KF-8004, KF-8675, and KF-8015 (all by Shin-Etsu Chemical Co., Ltd.); and amodimethicone emulsions such as SM8704C, SM8904, BY22-079, FZ-4671, and FZ-4672 (all by Dow corning Toray Co., Ltd.).

The total content of these silicones in the treatment composition of the present invention is usually 0.1 to 10%, preferably 0.2% to 7.5% and more preferably 0.5 to 5%, by weight calculated to the total of the composition.

The compositions may also include an organic conditioning oil. Suitable ones are selected from a hydrocarbon oil having at least 10 carbon atoms, a polyolefin, a fatty acid ester, a fatty acid amide and mixtures thereof.

Examples of the hydrocarbon oil include a cyclic hydrocarbon, a linear aliphatic hydrocarbon (saturated or unsaturated), and a branched aliphatic hydrocarbon (saturated or unsaturated), and polymers or mixtures thereof are also included. The linear hydrocarbon oil preferably has 12 to 19 carbon atoms. The branched hydrocarbon oil includes hydrocarbon polymers, and preferably has more than 19 carbon atoms.

The polyolefin is a liquid polyolefin, more preferably a liquid poly-α-olefin, and even more preferably a hydrogenated liquid poly-α-olefin. The polyolefin used herein is prepared by polymerizing an olefin monomer having 4 to 14 carbon atoms, and preferably 6 to 12 carbon atoms.

The fatty acid ester may be, for example, a fatty acid ester having at least 10 carbon atoms. Examples of such a fatty acid ester include esters having a hydrocarbon chain derived from a fatty acid and an alcohol (for example, monoesters, polyhydric alcohol esters, or di- and tricarboxylic acid esters). The hydrocarbon group of these fatty acid esters may have another compatible functional group such as an amide group or an alkoxy group as a substituent, or the hydrocarbon group may be covalently bonded to those functional groups. More specifically, an alkyl and alkenyl ester of a fatty acid having a fatty acid chain having 10 to 22 carbon atoms, a carboxylic acid ester of an aliphatic alcohol having an aliphatic chain derived from an alkyl and/or alkenyl alcohol having 10 to 22 carbon atoms, and a mixture thereof are suitably used. Specific examples of these preferred fatty acid esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate and dioleyl adipate.

Further suitable oil components are natural oils such as paraffin oil and natural triglycerides.

Suitable natural triglycerides are argan oil, shea butter oil, karite oil, olive oil, almond oil, avocado oil, ricinus oil, coconut oil, palm oil, sesame oil, peanut oil, sunflower oil, peach kernel oil, wheat germ oil, macadamia nut oil, macadamia oil, night primrose oil, jojoba oil, castor oil, soya oil, lanolin, passiflora oil, black cumin oil, borage oils, grapeseed oil, hempseed oil, kukui nut oil, and rosehip oil.

The organic conditioning oil may be used in combination of two or more kinds, and the total concentration is typically in the range of 0.1 to 10%, preferably 0.2% to 7.5% and more preferably 0.5 to 5%, by weight calculated to the total of the composition.

The compositions may also contain a fatty alcohol having 8 carbon atoms or more. Usually, the higher alcohol has 8 to 22 carbon atoms, and preferably 16 to 22 carbon atoms. Specific examples thereof include cetyl alcohol, stearyl alcohol, behenyl alcohol, and mixtures thereof.

The fatty alcohol may be used in combination of two or more kinds, and the content thereof is typically 0.1 to 10%, preferably 0.2% to 7.5% and more preferably 0.5 to 5%, by weight calculated to the total of the composition.

The thickening agents include any polymer either natural or synthetic thickening cosmetic compositions, especially aqueous compositions. Examples are cellulose and its derivatives such as hydroxyethylcellulose, guar and its derivatives such as hydroxypropyl guar. Additional examples are xanthan gum and its derivatives, acrylate polymers commercially available for example under the trade name Carbopol. In selection of the thickening agent, compatibility with any other components of the composition should carefully be examiner.

The thickening agents may be comprised in the range of 0.1 to 10%, preferably 0.2% to 7.5% and more preferably 0.25 to 5%, most preferably 0.5 to 2.5% by weight calculated to the total of the composition.

The compositions may contain one or more organic solvents such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of organic solvent can be in the range of 1 to 40%, preferably 1 to 25% by weight, calculated to total of the composition.

Additionally polyols may suitably be comprised in the compositions. Suitable ones are panthenol, glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxy-benzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2.2'-dihydroxy-4,4'-dimethoxy-5.5'-disulfobenzo-phenone or the sodium salt thereof, 2-hydroxy-4-octyloxybenzophenone, 2-hydroxy-4-methoxy-4'-methyl benzophenone, 3-benzyl-idenecampher, 3-(4'-sulfo)-benzyl-idenebornane-2-one and the salts thereof and/or 3-(4'-methyl benzylidene)-DL-campher, polysilicone-15. The preferred amount of the UV-absorber ranges from about 0.01% to 2.5%, more preferably from 0.05% to 1% by weight, calculated to the total of the composition.

The compositions comprising one or more of the above dye compounds may also comprise further dyes. They may be direct dyes or oxidative dye precursors and couplers.

Suitable direct dyes are cationic, anionic, neutral dyes and mixtures thereof as available commercially from various suppliers and used mainly in semi-permanent hair coloration.

One of the suitable direct dyes are cationic dyes. Non-limiting examples are Basic Blue 6, Basic Blue 7, Basic Blue 9, Basic Blue 26, Basic Blue 41, Basic Blue 99, Basic Brown 4, Basic Brown 16, Basic Brown 17, Basic Orange 31, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87, and their salts such as chloride, methosulfate, bromide etc. and mixtures thereof.

Further suitable direct dyes are anionic dyes. Suitable non-limiting examples are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium, and their mixtures.

Further suitable dyes for colouring hair within the meaning of the present invention are those of neutral nitro dyes. Suitable non-limiting examples are HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Plant dyestuffs may also be used as hair colorant within the meaning of the present invention for example henna (red or black), alkanna root, laccaic acid, indigo, logwood powder, madder root and rhubarb powder, etc.

It should be noted that the above dyestuffs are also suitable for use in mixture. In other words, cationic, anionic and nitro dyes are used in mixture within the meaning of the present invention. When using direct dyes of various categories, their compatibility must be taken into account.

Concentration of additional direct dyes in the compositions of the present invention is within the range of 0.001 to 5%, preferably 0.01 to 4% and more preferably 0.05 to 3%, and most preferably 0.1 to 2% by weight, calculated to total composition.

The pH of the composition of the present invention is in the range of 2 to 11, preferably 5 to 11, more preferably 6 to 11 and most preferably 6.8 to 10. The pH of the compositions may be adjusted using any organic and/or inorganic acids and alkalizing agents such as ammonium hydroxide and alkanolamines such as monoethanolamine or their mixtures.

Compositions of the present invention may be used after mixing with an oxidizing agent. The oxidizing agents suitable are hydrogen peroxide, urea peroxide, melamin peroxide and perborate salts. The most preferred is hydrogen peroxide. The concentration of the oxidizing agent is usually 2 to 12% by weight calculated to the total of the composition.

Composition of the present invention may comprise one or more oxidative dye precursor. In principal all oxidative dye precursors available for hair colouring purposes are suitable within the meaning of the present invention.

As a rule, it is possible to incorporate any developing substances known in the art. Special mention is made of p-phenylenediamine, p-aminophenol and substituted p-phenylenediamines such as 2,5-diamino-toluene, 2-n-propyl or 2-ethyl-p-phenylenediamine, 2,6-di-methyl-p-phenylene-diamine, 2-(2,5-diaminophenyl) ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, tetraamino pyrimidines, triaminohydroxy pyrimidines, diaminomono- and -dihydroxy pyrimidines, aminotriazines, 5-amino salicylic acid and/or 1,2,4-triamino benzene or the water-soluble salts thereof.

Further suitable ones aminopyridines are 2,5-diaminopyridine, 2,3-diaminopyridine, 2,6-diaminopyridine, 3-amino-2-methyl amino-6-methoxypyridine, 2-dimethyl-5-aminopyridine, 2-dimethyl aminoethyl-3-hydroxypyridine, 2-amino-4,6-dimethyl pyridine, 2-amino-3-hydroxypyridine, 3-amino-2(β-hydroxyethyl amino)-6-methoxy-pyridine, 2,6-dimethyl amino-5-aminopyridine, 2-di(hydroxyethyl) amino-5-aminopyridine, 2-hydroxyethyl amino-5-aminopyridine, 4-hydroxy-2,5,6-triaminopyrimidine and/or the water-soluble salts thereof.

Within the meaning of the present invention above mentioned developers can as well be present as a mixture of each other.

The total concentration of the dye precursors (developing substances) customarily ranges between 0.001 to 5%, preferably 0.01 to 4% and more preferably 0.05 to 3%, and most preferably 0.1 to 2% by weight, calculated to the total of the composition.

In a further embodiment of the present invention compositions comprise in addition to at least one oxidative dye precursor at least one coupling substance. As a rule any coupling substance customarily used in oxidative hair colouration area is suitable within the meaning of the present invention. Non-limiting coupling substances, are 5-amino-2-methylphenol, 2-methyl-5-hydroxyethylaminophenol, 2,4,-diamnophenoxyehanol, 2-amino-4-hydroxyethylaminoanisol, 2-methyl-5-amino-6-chlorphenol, 1,3-bis(2,4-diaminophenoxy)propane, 2-bis(2-hydroxyethyl)aminotoluene, 2-amino-5-methylphenol, resorcinol, 2-methyl-resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 1,3-diamino-benzene, 1-amino-3-(2'-hy-droxyethylamino)benzene, 1-amino-3-[bis(2'-hydroxy-ethyl) amino]benzene, α-naphthol, 4,6-dichlororesorcinol, 1,3-diaminotoluene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxy-ethyl amino)benzene or the water-soluble salts thereof. One or more of the above mentioned coupler can also be used in a mixture.

In the hair dyeing compositions according to the invention, the coupling substance(s) as reaction partners of the developing substance(s) are present in approximately the same molecular proportions as the developing substances, i.e. in amounts from 0.001 to 5%, preferably 0.01 to 4% and more preferably 0.05 to 3%, and most preferably 0.1 to 2% by weight, calculated to the total of the composition.

In further embodiment of the present invention, compositions comprise mixtures of the hair dyes mentioned above. In other words, a ready to use hair dyeing composition comprises at least one direct dye and at least one oxidative dye precursor, optionally at least one coupling substance in addition to the novel dyes of the present invention.

In a further embodiment of the present invention which may also be required because of the stability of the novel dyes of the present invention and/or stability of the other direct dyes, the composition comprising one or more novel dyes of the present invention and optionally one or more direct dyes is kept separate until the use from the composition comprising one or more oxidative dyes, and mixed immediately before use with each other and with a composition comprising one or more oxidizing agent. Therefore another object of the present invention is a process for colouring hair wherein a composition comprising one or more dyes of the present invention and optionally one or more additional direct dye is mixed with a composition comprising one or more oxidative dye precursors and optionally one or more coupling substances and a composition comprising one or more oxidizing agent, and applied onto hair and rinsed off from hair after leaving 1 to 45 min on the hair, the hair is optionally shampooed and dried.

In a further embodiment of the present invention, the composition is an anhydrous powder composition and comprises one or more novel dyes of the present invention, one or more persalts at a total concentration of 5 to 60%, preferably 10 to 60% and more preferably 20 to 50% by weight, calculated to the total of the composition and a powder alkalizing agent such as sodium metalsilicate. Such compositions are used to bleach and dye hair after mixing with an aqueous composition comprising one or more oxidizing agent.

SYNTHESIS OF DYES

Synthesis of Dye I: 7-((1,2,4-Thiadiazol-5-yl)diazenyl)-2-methylbenzo[b]thiophene-4-ol a) 4-(5-Methylthiophen-2-yl)-4-oxobutanoic acid 100 g (0.98 mol) 2-methylthiophen and 118 g (1.18 mmol) succinic acid anhydride are dissolved in 800 ml CH2Cl2. 287 g (2.16 mol) AlCl3 is added (temperature<=30° C.). After 15 min 500 g ice is added. The organic phase separated and the water phase 2× extracted with 150 ml ethyl acetate. The combined organic phases are evaporated to dryness and the product is recrystallized. Yield 86% b) 3-(5-Methylthiophene-2-yl)propanoic acid 105 g (0.053 mol) 4-(5-Methylthiophen-2-yl)-4-oxobutanoic acid are dissolved in 120 ml diethyleneglycol, 88 ml (1.96 mol) hydrazine hydrate und 101 g (1.8 mol) KOH. After 5 h under reflux 500 ml water and conc. HCl are added. Extraction and evaporation of diethyl ether gives a yield of 70%.

c) 2-Methyl-6,7-dihydrobenzo[b]thiophene-4(5H)-one 6.4 g (34.7 mmol) 3-(5-Methylthiophen-2-yl)propanoic acid is dissolved in 6 ml acetic anhydride and 1.4 ml ortho-phosphoric acid. After 3 h at 130° C. the mixture is poured on 400 ml water and neutralized. After extraction with CH2Cl2 and distillation a yellow oil is obtained, yield 97% d) 5-Bromo-2-methyl-6,7-dihydrobenzo[b]thiophene-4(5H)-one 27.3 g (0.16 mol) 2-Methyl-6,7-dihydrobenzo[b]thiophene-4(5H)-one is dissolved in 100 ml carbon tetrachloride und 600 ml diethyl ether and cooled to −10° C. Then 41.6 g (0.26 mol) bromine dissolved in 50 ml carbon tetrachloride is added dropwise. After 12 h the organic phase is evaporated and grey needles in 90% yield are received.

e) 2-Methylbenzo[b]thiophen-4-ol 2 g (7.87 mmol) 5-bromo-2-methyl-6,7-dihydrobenzo[b]thiophene-4(5H)-one, 1.16 g (15.74 mmol) Li2CO3 and 137 g (15.74 mmol) LiBr are suspended in 30 ml dry DMF and heated for 3 h under reflux. After extraction with ethyl acetate and evaporation 2-methylbenzo[b]thiophen-4-ol is obtained, yield 80%.

f) Dye I: 7-((1,2,4-Thiadiazol-5-yl)diazenyl)-2-methylbenzo[b]thiophene-4-ol 5 mmol 1,2,4-thiadiazol-5-amine is dissolved in 30 ml ortho-phosphoric acid under gentle warming followed by cooling to 0° C. and addition of 1 g NaNO2 getting a green solution. At −10° C. 2-methylbenzo[b]thiophene-4-ol dissolved in methanol is added and kept for 1 h at −10° C. followed by 12 h at 0° C. After purification by column chromatography (silica gel, eluent: n-heptane/ethyl acetate 1:1). The red-brown Dye I (yield 35%) is characterized by:
Melting point: 268-270° C., 1H NMR (250 MHz, DMSO): δ=8.83 (s, 1H), 8.38 (d, J=5.3 Hz, 1H), 8.27 (d, J=5.3 Hz, 1H), 3.90 (s, J=11.1 Hz, 3H), 3.84 (s, 3H) ppm. UV/Vis (DMSO)·max (lg □)=S: 476 nm (4.30); B: 528 nm (4.62).

Synthesis of Dye II: Ethyl-7-((1,2,4-thiadiazol-5-yl)diazenyl)-4-hydroxy-2-methylbenzo[b]thiophene-6-carboxylate a) Ethyl-4-acetoxy-2-methylbenzo[b]thiophene-6-carboxylate 70.5 g (0.63 mol) potassium t-butanolate are dissolved in 500 ml t-butanol. To the suspension a mixture of 26.5 g (0.21 mol) 5-methylthiophencarbaldehyde and 157 ml (0.95 mol) diethylsuccinate are added at RT and heated for 45 min under reflux. Then a further portion of potassium t-butanolate, diethylsuccinate and t-butanol in the above quantities is given and further heated for 45 min under reflux. The mixture is poured in 1 liter water and adjusted with conc. HCl to pH 2.

After filtration the solid material is washed with n-pentane and the water phase extracted 3× with 150 ml ethyl acetate. The organic phases are extracted 4× with 100 ml 10% Na2CO3 solution and the water phases 2× washed with 100 ml diethyl ether. With conc. HCl the pH is adjusted to 2 and further extraction with 4× 100 ml ethyl acetate is done. The organic extract is dried and evaporated to dryness.

The intermediate product is suspended in 500 ml acetic anhydride and heated with 206.7 g (2.52 mol) sodium acetate for 5 h under reflux. After evaporation the black product is extracted with a 1:1 mixture of n-pentane/n-heptane until no more educt is present. After keeping temperature overnight at 5° C. a yellow solid and a brown oil are separating. The yellow solid is used without further purification, yield 65%.

b) Ethyl 4-hydroxy-2-methyl-1-benzothiophene-6-carboxylate

A suspension of 3.21 g (11.5 mmol) ethyl-4-acetoxy-2-methylbenzo[b]thiophen-6-carboxylate and 1.6 g (11.5 mmol) K2CO3 in 20 ml ethanol is heated for 1-2 h under reflux until no educt is present (TLC-check: Rf=0.54, silica gel, n-Heptan/ethyl acetate 2:1).

After filtrating and washing with ethanol the product is dried and 300 ml water is added. After adding conc. HCl bringing pH to 2 the water phase is extracted 3× with 100 ml ethyl acetate. Drying and evaporation gives a brown oil which is recrystallized from n-heptane/ethyl acetate to give brown needles. Yield 31% c) Dye II: Ethyl-7-((1,2,4-thiadiazol-5-yl)diazenyl)-4-hydroxy-2-methylbenzo[b]thiophene-6-carboxylate In a beaker 10 mmol 1,2,4-thiadiazol-5-amine is dissolved in 26 ml glacial acetic acid and 14 ml propanoic acid followed by cooling to −10° C. 10 ml sulfuric acid is added dropwise to keep the temperature below −5° C. Then 8 ml of a 2 M nitrosyl sulfuric acid is added at −10° C. and stirred for 1 h at −10° C. Excess of nitrosating agent is destroyed by adding 0.5 g urea.

10 mmol of Ethyl 4-hydroxy-2-methyl-1-benzothiophene-6-carboxylate is dissolved in 200 ml methanol and cooled to −10° C. To this solution the diazonium salt solution is added (temperature maximum −5° C.) followed by further stirring at −10° C. for 1 h and overnight keeping at 0° C.

A red brown solid is obtained, yield 88%. Melting point: 199-201° C. 1H NMR (250 MHz, DMSO): δ=8.96 (s, 1H), 7.33 (s, 1H), 7.15 (s, 1H), 4.40 (q, J=7.1 Hz, 2H), 2.58 (s, 3H), 1.36 (t, J=6.6 Hz, 3H) ppm. UV/Vis (DMSO) ∟ max (lg ∣ )=S: 481 nm (4.27); B: 532 nm (4.73).

Synthesis of Dye III: 2-Methyl-7-(thiazol-2-yldiazenyl)benzo[b]thiophene-4-ol a) 2-Methylbenzo[b]thiophen-4-ol Preparation is given in the synthesis steps of Dye I a-e.

b) Dye III: 2-Methyl-7-(thiazol-2-yldiazenyl)benzo[b]thiophene-4-ol 1,3-Thiazol-2-amine (10 mmol) is dissolved in 26 ml glacial acetic acid and 14 ml propanoic acid followed by cooling to −10° C. 10 ml sulfuric acid is added dropwise to keep the temperature below −5° C. Then 8 ml of a 2 M nitrosyl sulfuric acid is added at −10° C. dropwise. After stirring for 1 h at −10° C. the excess of nitrosating agent is destroyed by adding 0.5 g urea.

10 mmol 2-Methylbenzo[b]thiophene-4-ol is dissolved in 200 ml methanol and cooled to −10° C. The diazonium salt from a) is added dropwise, keeping temperature below −5° C. After 1 h stirring at −10° C. and keeping overnight at 0° C. the precipitated Dye III is filtered, washed with water, dried and recrystallized giving brown to orange needles, yield: 76%. Melting Point: 234° C. 1H NMR (250 MHz, DMSO): ∟=11.54 (s, 1H), 8.08. 7.96 (m, 2H), 7.78 (d, J=3.3 Hz, 1H), 7.30 (d, J=1.0 Hz, 1H), 7.03 (d, J=8.4 Hz, 1H), 2.57 (s, 3H) ppm. UV/Vis (DMSO) ∟ max (lg ∟ )=S: 460 nm (4.31); 526 nm (4.61).

Synthesis of Dye IV: 4((4-(Dimethylamino)-2-(ethoxycarbonyl)benzo[b]thiophene-7-yl)diazenyl)-1-methylpyridin-1-ium methylsulfate a) 2,6-Difluorobenzaldehyde 34.8 g (0.6 mol) KF is dissolved in 250 ml sulfolan under nitrogen for 2 h at 100° C. By azeotropic distillation water is removed. 20 g (0.11 mol) 2,6-dichlorobenzaldehyde and 2.8 g (6.68 mmol) tetraphenyl phosphoniumbromide are given to the water-free mixture and heated overnight to 180° C. The resulting dark solution is filtered, the solid washed with ethyl acetate and the low-boiling components removed by water pressure evaporation. By vacuum distillation (24 mbar, 85-86° C.) the colorless product is obtained, yield 77% b) 2-(Dimethylamino)-6-fluorobenzaldehyde 29.2 g (0.21 mol) 2,6-difluorobenzaldehyde and 42.7 g (0.31 mol) K2CO3 are given into 24 ml DMF and 39 ml (0.31 mol) dimethylamine solution (40% in water) is added dropwise. After 2 h at 40-50° C. the solution is poured into 400 ml of water and is extracted 3× with 100 ml ethyl acetate. The total organic phase is washed 2× with 100 ml brine, dried, evaporated to give a yellow oil which is cooled to 5° C. finally giving yellow needles. Yield 92% c) Ethyl-4-(dimethylamino)benzo[b]thiophene-2-carboxylate 19.2 g (0.12 mol) 2-(dimethylamino)-6-fluorobenzaldehyde and 18.9 ml (0.17 mol) ethyl thioglycolic acid ester are dissolved in 72 ml dry DMF and 6.9 mg (0.29 mol) NaH (60% ig in mineral oil) is added in portions under ice cooling.

After 3 h the mixture is poured on 600 ml water and 3× extracted with 150 ml ethyl acetate. After washing 2× with brine, drying and evaporating the purification is done by flash chromatography (silica gel, n-heptane/ethyl acetate 20:1). At 5° C. yellow crystals are obtained, yield 85% d) Ethyl-4-(dimethylamino)-7-(pyridine-4-yldiazenyl)benzo[b]thiophene-2-carboxylate Pyridin-4-amine (10 mmol) is dissolved in 26 ml glacial acetic acid and 14 ml propanoic acid followed by cooling to −10° C. 10 ml sulfuric acid is added dropwise to keep the temperature below −5° C. Then 8 ml of a 2 M nitrosyl sulfuric acid is added at −10° C. dropwise. After stirring for 1 h at −10° C. the excess of nitrosating agent is destroyed by adding 0.5 g urea.

10 mmol ethyl 4-(dimethylamino)-1-benzothiophene-2-carboxylate is dissolved in 200 ml methanol and cooled to −10° C. The above diazonium salt solution is added dropwise, keeping temperature below −5° C. After 1 h stirring at −10° C. and keeping overnight at 0° C. ammonium acetate and water are given to the reaction solution. Then 3× 100 ml of ethyl acetate is used for extraction. After 3× washing with brine, drying and evaporation the crude ethyl-4-(dimethylamino)-7-(pyridine-4-yldiazenyl)benzo[b]thiophene-2-carboxylate is separated by column chromatography (silica gel, n-heptane/ethyl acetate 1:1). A red solid is obtained, yield 53% e) Dye IV: 4-((4-(Dimethylamino)-2-(ethoxycarbonyl)benzo[b]thiophene-7-yl)diazenyl)-1-methylpyridin-1-ium methylsulfate 80 mg (0.23 mmol) Ethyl-4-(dimethylamino)-7-(pyridine-4-yldiazenyl)benzo[b]thiophene-2-carboxylate is dissolved in DMF and treated with an excess of dimethylsulfate at 50° C. until no educt is detectable. Recrystallisation from methanol gives Dye IV. A blue-black solid, yield 83%. Melting Point 199-201° C.

1H NMR (400 MHz, DMSO): δ=8.74 (d, J=4.2 Hz, 2H), 8.39 (d, J=1.9 Hz, 1H), 8.17 (dd, J=8.7, 2.0 Hz, 1H), 7.71 (d, J=4.2 Hz, 2H), 7.02 (dd, J=8.8, 1.9 Hz, 1H), 4.38 (tt, J=7.0, 3.6 Hz, 2H), 3.36 (d, J=1.9 Hz, 6H), 3.13 (s, 9H), 1.37 (td, J=7.0, 2.0 Hz, 3H) ppm. UV/Vis (DMSO) ∟ max (lg ∟)=568 nm (4.72).

EXAMPLE COMPOSITIONS-1

| | % by weight active matter | | | |
|---|---|---|---|---|
| | A | B | C | D |
| 2-propanol | 5.00 | 5.00 | 5.00 | 5.00 |
| Ammonia | 1.25 | 1.25 | 1.25 | 1.25 |
| Dyestuff I | 0.40 | — | — | — |
| Dyestuff II | — | 0.40 | — | — |
| Acid red 33 | — | — | 0.40 | — |
| Acid red 52 | — | — | — | 0.40 |
| Water | to 100 | to 100 | to 100 | to 100 |

The pH of the compositions A to D was adjusted with HCl to 10.

Method 1: Composition A to D was applied onto white goat hair for 30 min at 30° C. Then the hair was rinsed, shampooed, dried and the dyeing result was determined colorimetrically by measuring L, a, and b values using a laboratory colorimeter. The Delta E values were calculated as the vectoral differences.

Method 2: Hair dyeing was carried out by applying the above composition after mixing with a 50% hydrogen peroxide comprising composition to produce an active hydrogen peroxide concentration of 3%, onto goat hair and being left on the hair for 30 min at 30° C. and rinsed off from hair with water and hair was shampooed and dried and the color was measured.

Method 3: Permed goat hair was dyed with the above compositions onto hair and after leaving the composition on the hair for 30 min at 30° C., the hair was rinsed off and shampooed and dried. The Color was measured with a laboratory colorimeter.

Following results were obtained:

| | Composition | | | |
|---|---|---|---|---|
| | A | B | C | D |
| Method 1 | 70 | 71 | 49 | 49 |
| Method 2 | 73 | 73 | 51 | 53 |
| Method 3 | 71 | 74 | 69 | 76 |

From the above results it is clear that the compositions A and B colour hair tresses under non-oxidative (Method 1) and oxidative conditions (Method 2) in the same intensity. The hair tress damaged by means of permanent shaping treatment (Method 3) is also colored in the same intensity. On the other hand the compositions based on the existing dyes do show variability in coloring hair under oxidative condition and also color intensity on damaged hair is much stronger the natural hair which clearly indicates that hair comprising damaged parts may not be colored homogeneously with the known dyes but colored homogeneously with the novel dyes of the present inventions.

EXAMPLE COMPOSITIONS-2

| | % by weight active matter | | | | | | | |
|---|---|---|---|---|---|---|---|---|
| | E | F | G | H | I | J | K | L |
| 2-propanol | 5.00 | 1.25 | 1.67 | 5.00 | 5.00 | 5.00 | 5.00 | 5.00 |
| Ammonia | 1.25 | 0.31 | 0.42 | 1.25 | 1.25 | 1.25 | 1.25 | 1.25 |
| Dyestuff I | 0.40 | 0.10 | | | 0.10 | 0.30 | | |
| Dyestuff II | | | 0.13 | 0.10 | | | | |
| Dyestuff III | | | | | | | 0.40 | |
| Dyestuff IV | | | | | | | | 0.40 |
| Basic Yellow 87 | | | | 0.30 | | | | |
| 2-Amino-6-chloro-4-nitrophenol | | | | | 0.30 | | | |
| Acid Violet 43 | | | | | | 0.10 | | |
| Xanthan Gum | 2.00 | 0.50 | | | | | | |
| Goldwell Topchic 6N | | 25.0 | | | | | | |
| Goldwell Topchic 6% Lotion | | 50.0 | 33.3 | | | | | |
| Goldwell Oxycur Platin Lightening Powder | | | 33.3 | | | | | |
| Water | to 100 | to 100 | to 100 | to 100 | to 100 | to 100 | to 100 | to 100 |

The invention claimed is:

1. A Compound according to the general structure

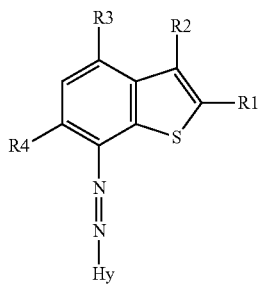

wherein R₁ is H, $C_1$-$C_4$ alkyl, $C_1$-$C_4$ hydroxyalkyl, COOH or COOR₅ wherein R₅ is $C_1$-$C_4$ alkyl, R₂ is H or NR₆R₇ wherein R₆ and R₇ are same or different H, $C_1$-$C_4$ alkyl, $C_1$-$C_4$ hydroxyalkyl or acetyl, R₃ is H, OH, NR₆R or NHSO₂R₈ wherein R₈ is NR₆R alkyl or NR₆R hydroxyalkyl, R₄ is H, COOH or COOR₅ and Hy is a heterocyclic group which is bound at a C atom to the diazo group and which may be substituted or unsubstituted, and is selected from the group consisting of

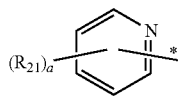 A-1

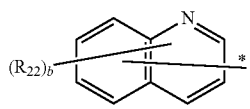 A-2

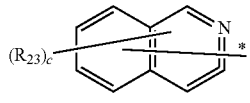 A-3

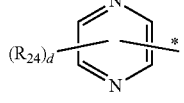 A-4

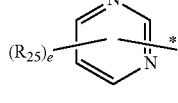 A-5

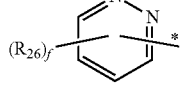 A-6

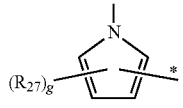 A-7

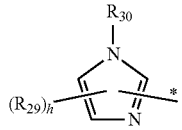 A-8

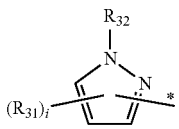 A-9

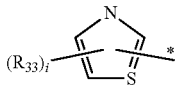 A-10

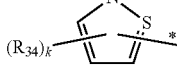 A-11

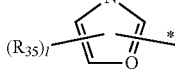 A-12

 A-13

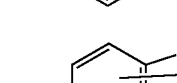 A-14

 A-15

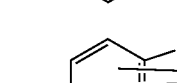 A-16

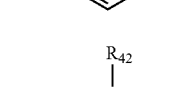 A-17

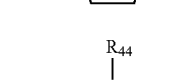 A-18

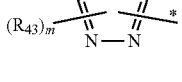 A-19

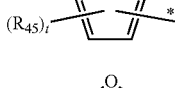 A-20

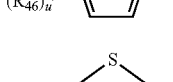 A-21

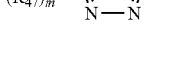 A-22

A-23

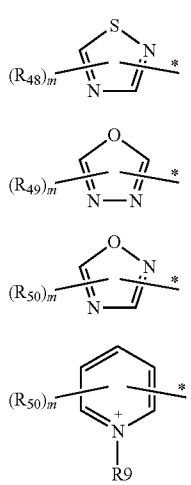

A-24

A-25

A-26 wherein R₉ is $C_1$-$C_4$ alkyl or $C_1$-$C_4$ hydroxyalkyl and "*" expresses position at which group binds to the diazo group, $R_{21}$ to $R_{50}$ independently represent hydrogen atom or a substituent which is selected from halogen atom, alkyl group, aryl group, hetero-ring group, cyano group, hydroxyl group, nitro group, alkoxy group, aryloxy group, amino group (including anilino group), acylamino group, aminocarbonylamino group, alkoxycarbonylamino group, alkylsulfonylamino group, arylsulfonylamino group, alkylthio group, arylthio group, hetero-ring thio group, sulfamoyl group, alkylsulfonyl group, arylsulfonyl group, acyl group, alkoxycarbonyl group, and carbamoyl group; the substituent is halogen atom, alkyl group, cyano group, hydroxyl group, nitro group, alkoxy group, amino group (including anilino group), acylamino group, alkylsulfonylamino group, and carbamoyl group, "a, p, q, r, s" represent an integer of 0 to 4, "b, c" represent an integer of 0 to 6, "d, e, f, g, t, u" represent an integer of 0 to 3, "h, i, j, k, l, o" represent an integer of 0 to 2, "m" represent an integer of 0 to 1, when "a" to "u" represent an integer of 2 or more and may be the same or different to each other.

2. The compound according to claim 1 wherein the Hy is selected from the group consisting of (A-1), (A-5), (A-8), (A-9), (A-10), (A-11), (A-12), (A-13), (A-14), (A-15), (A-17), (A-19), (A-22), (A-23), (A-24), (A-25) and (A-26).

3. The compound according to claim 1 wherein the compound has the structure chosen from the group consisting of

D-1

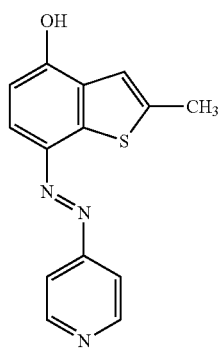

D-2

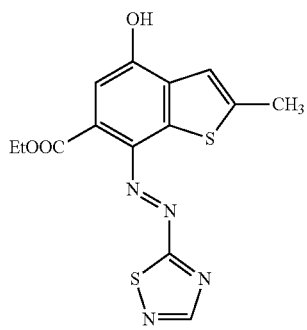

D-3

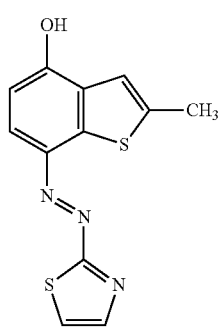

D-4

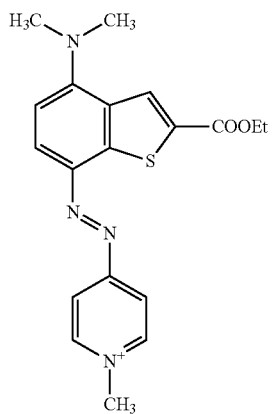

D-5

D-6
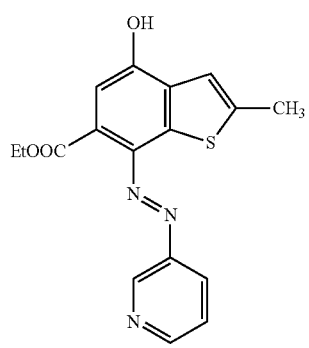
D-7
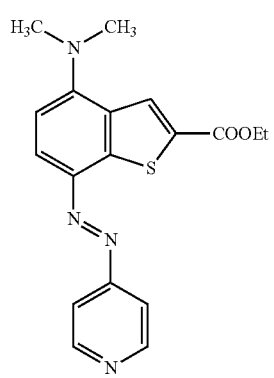
D-8
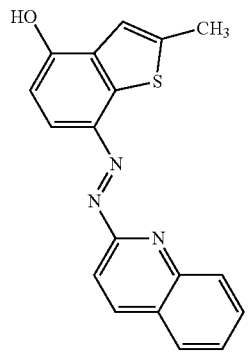
D-9
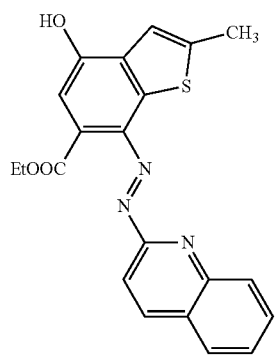
D-10
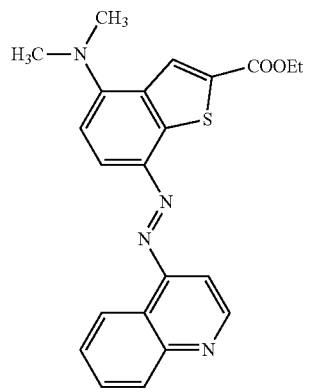
D-11
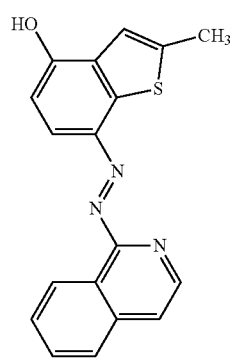
D-12
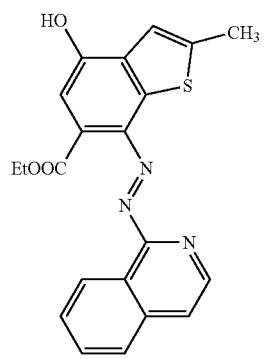
D-13
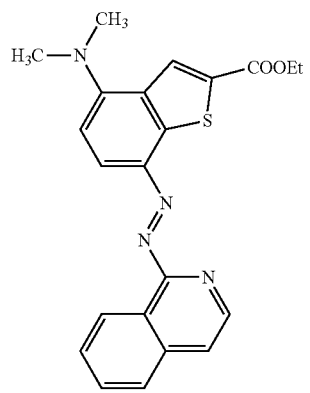

D-14
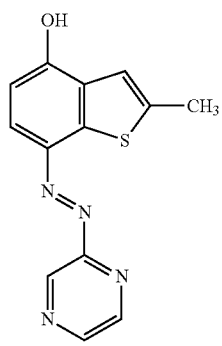
D-15
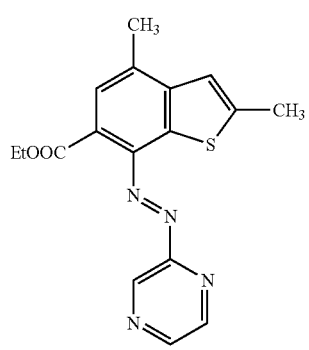
D-16
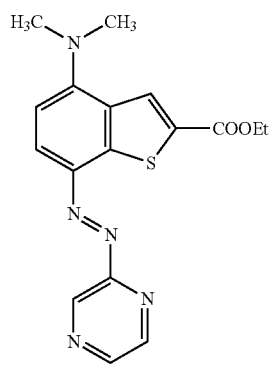
D-17
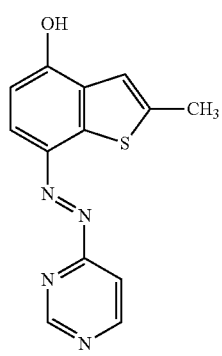
D-18
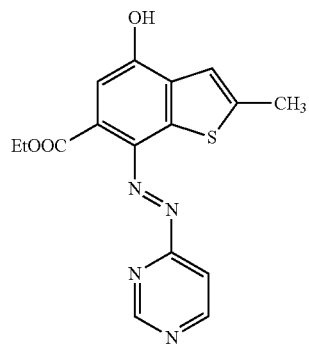
D-19
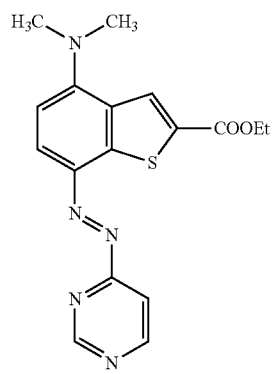
D-20
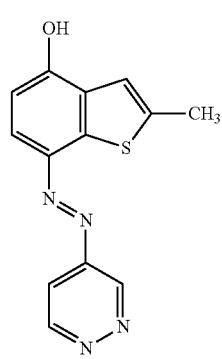
D-21
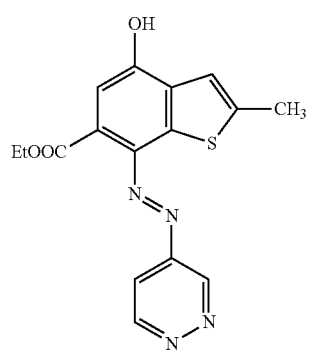

D-22 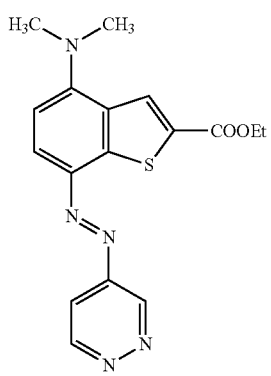
D-26 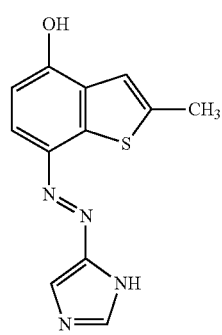
D-23 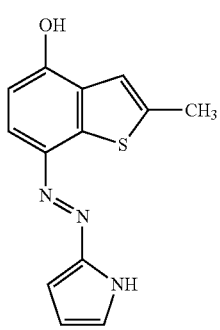
D-27 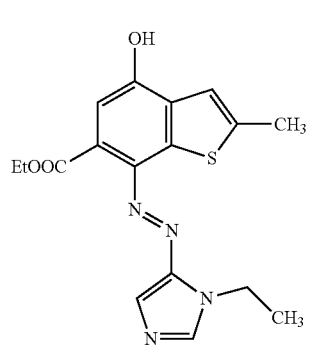
D-24 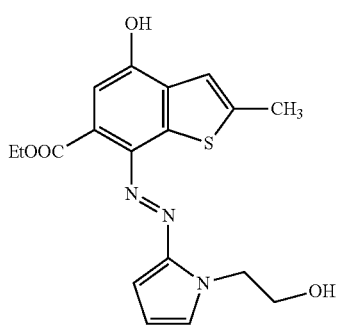
D-28 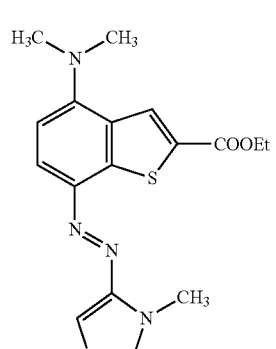
D-25 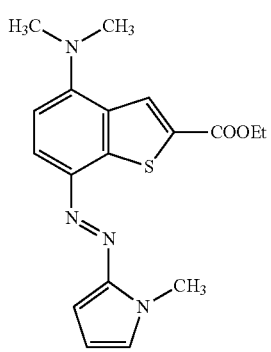
D-29 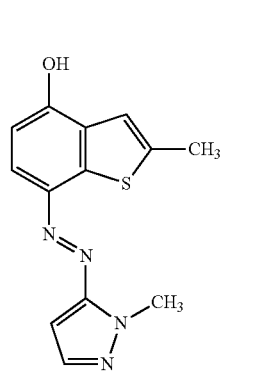

D-30 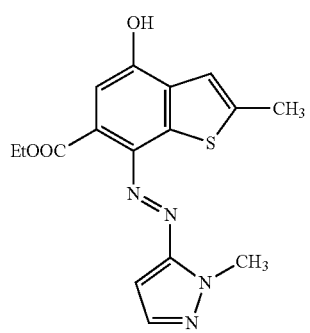
D-34 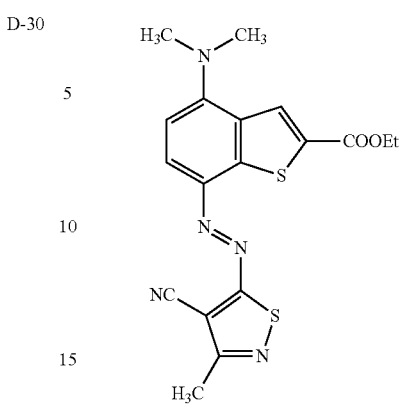
D-31 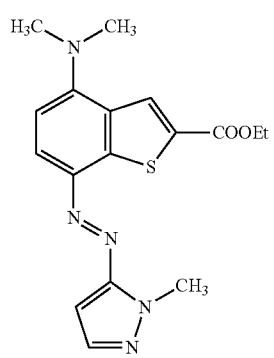
D-35 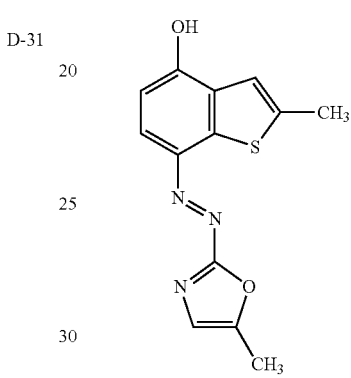
D-32 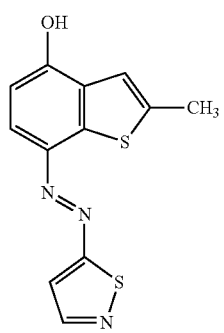
D-36 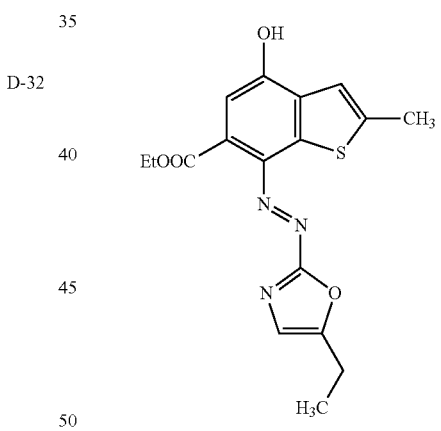
D-33 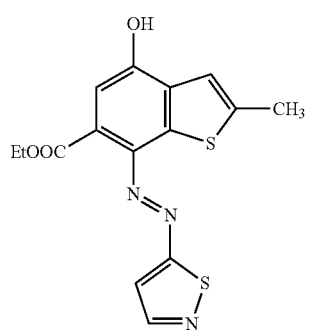
D-37 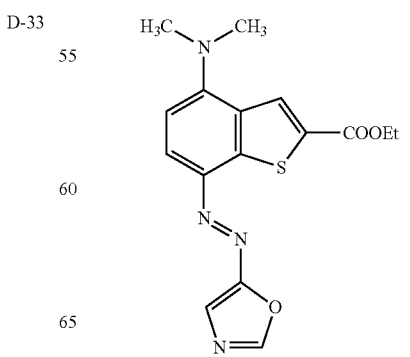

D-38
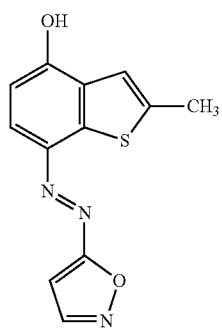
D-39
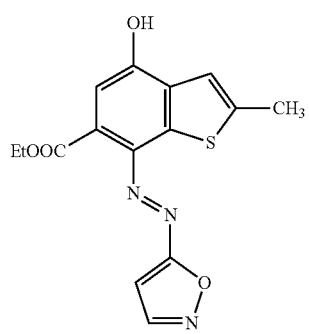
D-40
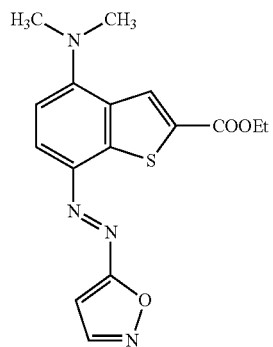
D-41
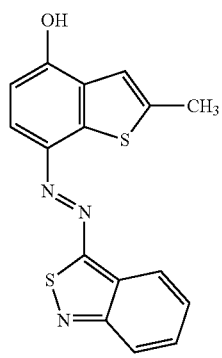
D-42
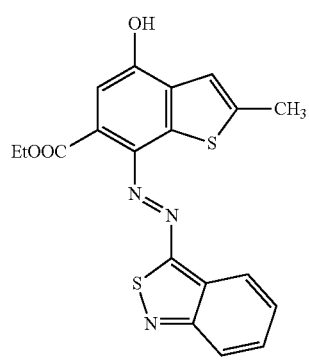
D-43
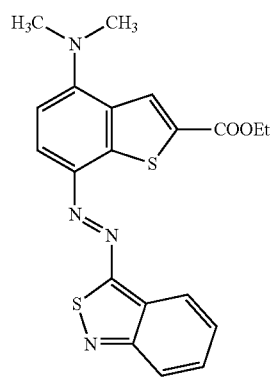
D-44
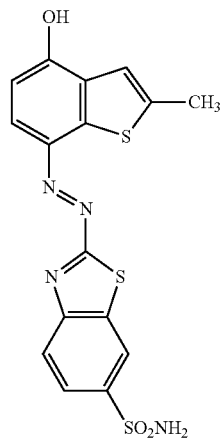
D-45
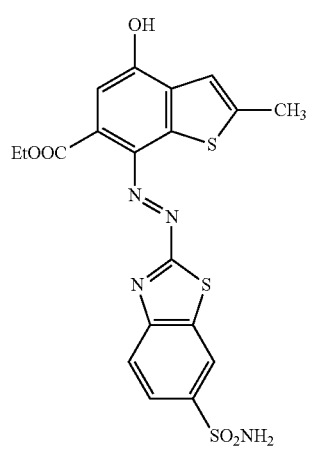

D-46 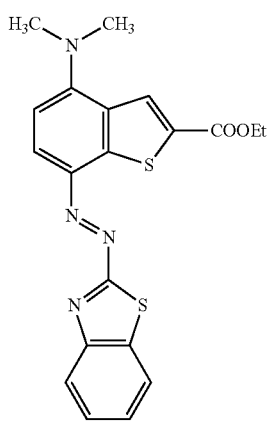
D-47 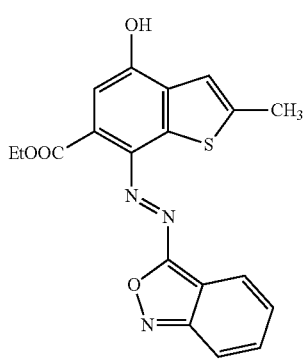
D-48 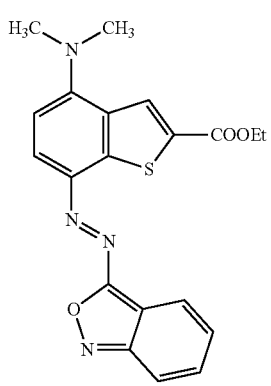
D-50 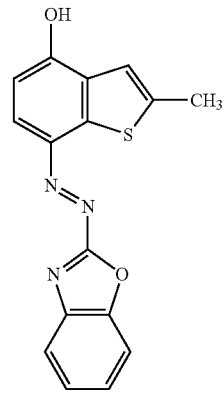
D-51 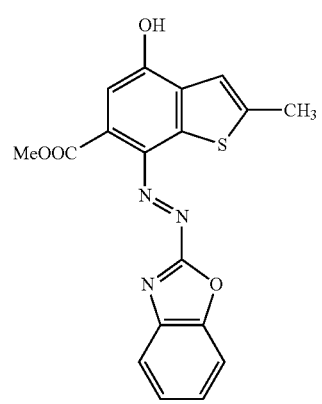
D-52 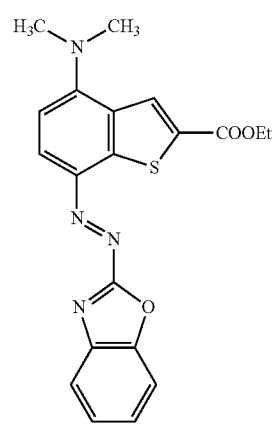
D-53 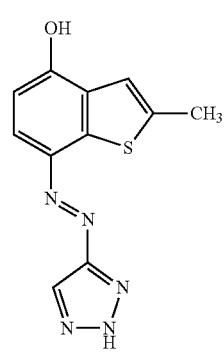

D-54 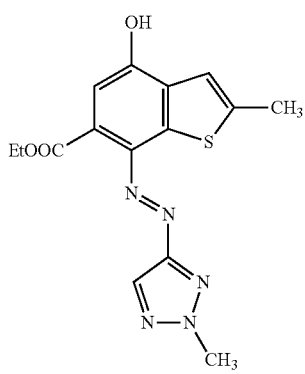
D-55 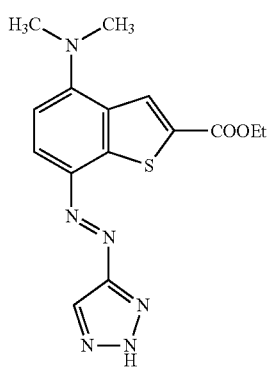
D-56 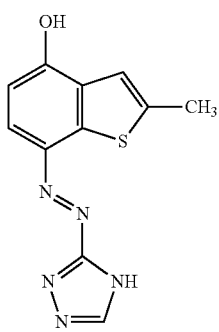
D-57 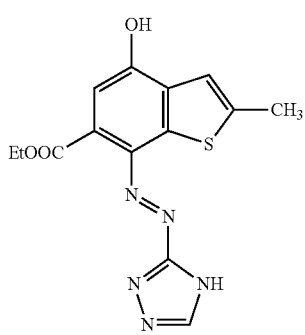
D-58 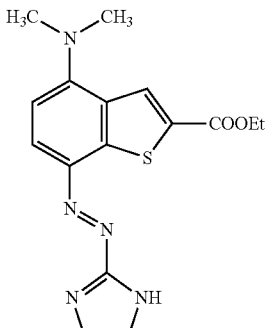
D-59 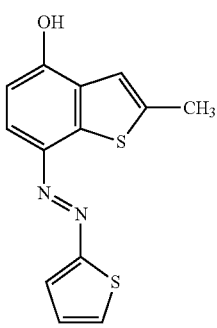
D-60 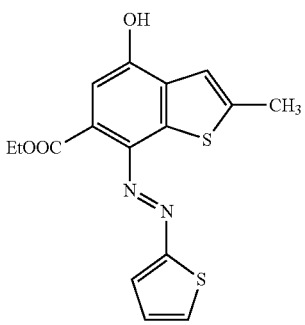
D-61 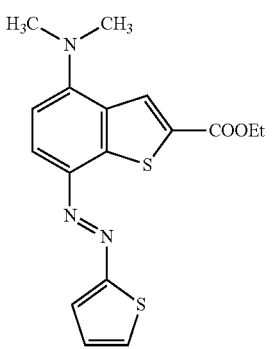
D-62

-continued
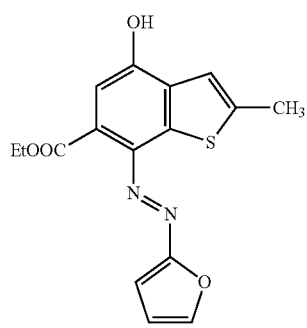
D-63
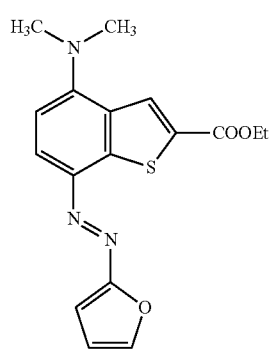
D-64
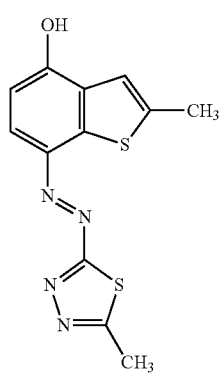
D-65
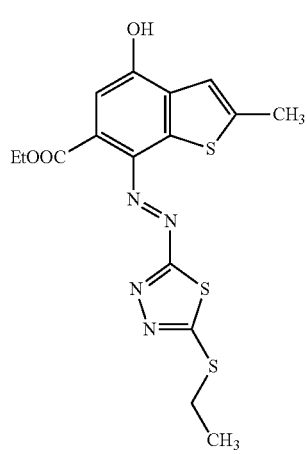
D-66
-continued
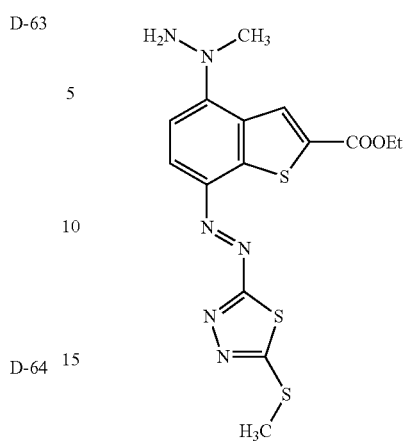
D-67
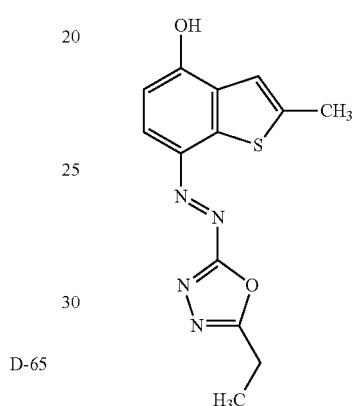
D-68
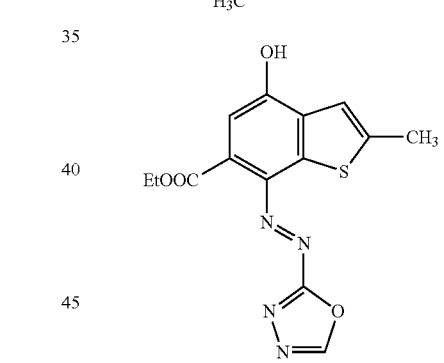
D-69
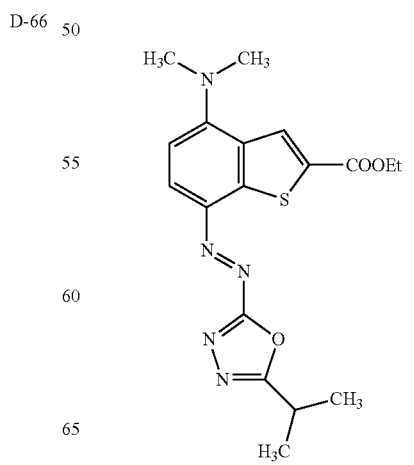
D-70

D-71 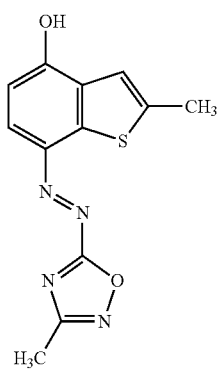

D-72 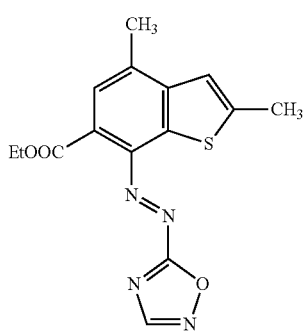

D-73 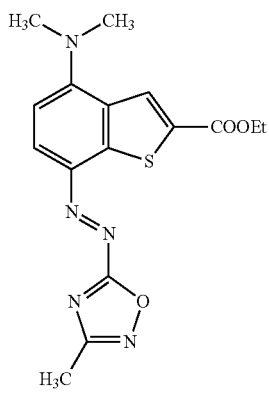

D-74 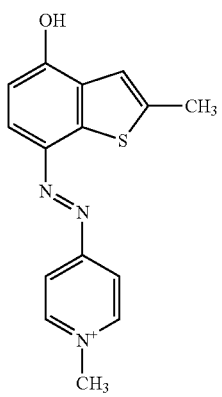

D-75 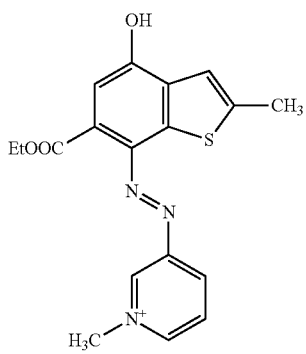

D-76 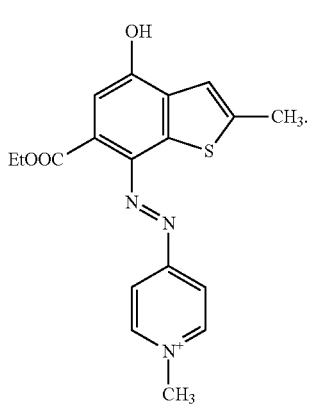

4. The compound according to claim 3 wherein the compounds are selected from D-1, D-2, D-3 and D4.

5. A composition characterized in that it comprises one or more of the compounds according to claim 1.

6. The composition according to claim 5 characterized in that it comprises one or more surfactants selected from anionic, nonionic, cationic and amphoteric ones.

7. The composition according to claim 5 characterized in that it comprises one or more cationic surfactant selected from the compounds or the general structure

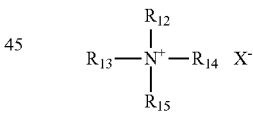

where $R_{12}$ is saturated or unsaturated, branched or straight alkyl chain with 8-22 C atoms or $R_{16}$ CO NH($CH_2$)$n$ where $R_{16}$ is saturated or unsaturated, branched or straight alkyl chain with 7-21 C atoms and n has typical value of 1-4 or $R_{16}$CO O($CH_2$)$n$ where $R_{16}$ is saturated or unsaturated, branched or straight alkyl chain with 7-21 C atoms and n has typical value of 1-4, and $R_{13}$ is a saturated or unsaturated, branched or straight alkyl chain with 1-22 C atoms or $R_{16}$CO NH($CH_2$)$n$ where $R_{16}$ is saturated or unsaturated, branched or straight alkyl chain with 7-21 C atoms and n has typical value of 1-4 or $R_{16}$ CO O($CH_2$)$n$ where R16 is saturated or unsaturated, branched or straight alkyl chain with 7-21 C atoms and n has typical value of 1-4, and R14 and R15 are independent from each other lower alkyl chain with 1 to 4 carbon atoms or ethoxy or propoxy group with number of ethoxy or propoxy groups varying in the range of 0 to 4, and X is chloride, bromide or methosulfate.

8. The composition according to claim 5 it comprises one or more hair conditioning compound, selected from cationic polymers, silicones, fatty alcohols, and conditioning oils.

9. The composition according to claim 5 characterized in that it comprises one or more organic solvent.

10. The composition according to claim 5 characterized in that it comprises one or more additional direct dyes selected from anionic, cationic and nonionic ones.

11. The composition according to claim 5 characterized in that it comprises one or more oxidizing agent.

12. The composition according to claim 5 characterized in that it comprises one or more oxidative dye precursors and optionally one or more coupling agents.

13. The compound according to claim 1 wherein the Hy is selected from the group consisting of A-10), (A-11), (A-12), (A-14), (A-22), (A-23), (A-25) and (A-26).

14. The compound according to claim 1 wherein the Hy is selected from the group consisting of (A-10), (A-23) and (A-26).

15. The compound according to claim 3 wherein the compound is selected from D2 and D3.

\* \* \* \* \*